US007008779B1

(12) United States Patent
Afar et al.

(10) Patent No.: US 7,008,779 B1
(45) Date of Patent: Mar. 7, 2006

(54) PHELIX: A TESTIS-SPECIFIC PROTEIN EXPRESSED IN CANCER

(75) Inventors: Daniel E. Afar, Pacific Palisades, CA (US); Rene S. Hubert, Los Angeles, CA (US); Arthur B. Raitano, Los Angeles, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 09/389,000

(22) Filed: Aug. 31, 1999

Related U.S. Application Data

(60) Provisional application No. 60/098,610, filed on Aug. 31, 1998, and provisional application No. 60/106,524, filed on Oct. 31, 1998.

(51) Int. Cl.
*C12H 15/00* (2006.01)

(52) U.S. Cl. .................. 435/69.1; 435/70.1; 530/387.1; 530/350; 424/184.1; 424/185.1; 536/23.1

(58) Field of Classification Search ................ 435/69.1, 435/70.1, 325, 7.1; 530/387.1, 350; 424/184.1, 424/185.1; 536/23.1; 514/2
See application file for complete search history.

(56) References Cited

FOREIGN PATENT DOCUMENTS

| EP | 0228243 A | 7/1987 |
|---|---|---|
| WO | WO/9523874 A | 9/1995 |
| WO | WO/9621671 A | 7/1996 |
| WO | WO 00/12709 | 3/2000 |

OTHER PUBLICATIONS

Reigen et al. Glossary of Genetics & Up to Genetics, Classical & Mol, 4th ed, Springer–Verlag, Berlin, p. 17, 1976.*
Grira. Science, 278: 1041–1042, 1997.*
Jair, Sci, Am. 271: 58–65, 1994.*
Curti Cut. Rev. Oncol/Hematol. 14: 29–39, 1993.*
Hartwell. Science 278: 1064–1068, 1997.*
Ezzell. J. NIH Res. 7: 46–49, 1995.*
Spitler. Cancer Biotherapy, 10: 1–3, 1995.*
Alberts, Mol. Biol. Cel, 3rd ed., p. 465, 1994.*
Shautz. Intl J Biochem Cell Biol 31:107–122, 1999.*
McClean. Eur. J. Cancer, 29A: 2243–2248, 1993.*
Bowie. Science, 257: 1306–1310, 1990.*
Bork. Genome Res. 10: 398–400, 2000.*
Scott. Nature Genetics 21: 440–443, 1999.*
Bauki. JBC 269 (4): 2847–51, 1994.*
MPSRCH Kauli Report, p. 2, 7, 2001.*
Roitt. Immunology, 4th ed., Mosby, London, p. 7.7–7.8, 7.9, 1998.*
Herbert. The Dictionary of Immunol., Acad. Press, 4th ed, p. 58, 1995.*
Greenspan. Nature Biotech 7: 936–937, 1999.*
Hillier et al., "zt61d10.r1 Soares testis NHT *Homo sapiens* cDNA clone 726835 5'," EMBL Database—EMEST24 Online! Entry HS1196684, Acc. No. AA293855, Apr. 22, 1997, XP002131732, the whole document.
Hillier et al., "zv04a08.r1 Soares NhHMPu S1 *Homo sapiends* cDNA clone 752630 5'," EMBL Database—EMEST24 Online! Entry HS1213074, Acc. No. AA417643, May 14, 1997, XP002131733, the whole document.
Wilson, Apr. 12, 1995, dbEST Id: 183622, GenBank Acc: R13043.
Adams et al., Apr. 21, 1997, dbEST Id: 980666, GenBank Acc: AA339260.
Wilson, Aug. 12, 1997, dbEST Id: 1039766, GenBank Acc: AA398348.
Klein et al., Nature Med. (1997) 3:402–408.
Morton and Myszka, Methods in Enzymology (1998) 295:268.
Muller et al., MCB (1991) 11:1785.
Pemberton et al., J. of Histochemistry and Cytochemistry (1997) 45:1697–1706.
Walter et al., Nat. Genetics (1994) 7:22.
Welch et al., Int. J. Cancer (1989) 43:449–457.
Welford, Opt. Quant. Elect. (1991) 23:1.

* cited by examiner

*Primary Examiner*—Susan Ungar
*Assistant Examiner*—Minh Tam Davis
(74) *Attorney, Agent, or Firm*—Morrison & Foerster LLP

(57) ABSTRACT

Described is a novel gene and its encoded basic Helix Loop Helix protein, termed PHELIX, and to diagnostic and therapeutic methods and compositions useful in the management of various cancers which express PHELIX, particularly including prostate cancer, bladder cancer, ovarian cancer and testicular cancer. In human normal tissues, PHELIX is only expressed in testis tissue. However, PHELIX is expressed at high levels in prostate cancer cells and in other cancer cells. The structure of PHELIX suggests that it may function as a transcription factor that normally exhibits a testis-specific expression pattern but is turned on in prostate cancer as well as in other cancers.

10 Claims, 11 Drawing Sheets

```
              11          20          29          38          47          56
5' GAC CGG GGG GCG GTT GGG GTT CAC CGC CTC GTG CCG TAC TGG CTT CTG GGT GGC
   --- --- --- --- --- --- --- --- --- --- --- --- --- --- --- --- --- ---
              65          74          83          92         101         110
   CCT TAA TGT CTT GTG CTC TAA GGT GCT GAG GGG AAA GAC GCG GGA GGT CTC TGG
   --- --- --- --- --- --- --- --- --- --- --- --- --- --- --- --- --- ---
             119         128         137         146         155         164
   CCT GAC ACT ATG AAG GAA GAG AGA AAC TAC AAC TTC GAC GGT GTG AGC ACC AAC
   --- --- --- --- --- --- --- --- --- --- --- --- --- --- --- --- --- ---
             173         182         191         200         209         218
   CGC CTG AAA CAG CAG TTG CTG GAA GAA GTC CGC AAG AAG TAG TGA ATG GAA AAC
   --- --- --- --- --- --- --- --- --- --- --- --- --- --- --- --- --- ---
             227         236         245         254         263         272
   CCG TTA TGA GAC ACA ACT TGA ATT AAA TGA TGA ACT AGA AAA GCA AAT TGT TTA
   --- --- --- --- --- --- --- --- --- --- --- --- --- --- --- --- --- ---
             281         290         299         308         317         326
   TCT CAA GGA GAA AGT GGA AAA AAT CCA TGG AAA CTC TTC AGA TAG ACT ATC TTC
   --- --- --- --- --- --- --- --- --- --- --- --- --- --- --- --- --- ---
             335         344         353         362         371         380
   TAT TCG TGT CTA TGA ACG AAT GCC AGT GGA ATC CTT AAA CAC ATT ACT TAA ACA
   --- --- --- --- --- --- --- --- --- --- --- --- --- --- --- --- --- ---
             389         398         407         416         425         434
   GCT AGA AGA AGA AAA GAA GAC TCT TGA AAG TCA AGT GAA ATA CTA TGC ACT TAA
   --- --- --- --- --- --- --- --- --- --- --- --- --- --- --- --- --- ---
             443         452         461         470         479         488
   ACT GGA ACA AGA ATC AAA GGC TTA CCA GAA GAT CAA CAA TGA ACG CCG TAC ATA
   --- --- --- --- --- --- --- --- --- --- --- --- --- --- --- --- --- ---
             497         506         515         524         533         542
   CCT AGC TGA AAT GTC TCA GGG TTC TGG TTT ACA TCA AGT TTC TAA AAG GCA ACA
   --- --- --- --- --- --- --- --- --- --- --- --- --- --- --- --- --- ---
             551         560         569         578         587         596
   GGT GGA TCA ACT GCC TAG GAT GCA AGA GAA TCT AGT GAA AAC GCA AAA ATA GAC
   --- --- --- --- --- --- --- --- --- --- --- --- --- --- --- --- --- ---
             605         614         623         632         641         650
   ATC TTA TTA GTT GGA GAT GTC ACT GTG GGC TAC CTG GCT GAT ACT GTA CAG AAA
   --- --- --- --- --- --- --- --- --- --- --- --- --- --- --- --- --- ---
             659         668         677         686         695         704
   CTA TTT GCA AAC ATA GCA GAA GTC ACC ATC ACC ATC AGT GAC ACG AAG GAG GCA
   --- --- --- --- --- --- --- --- --- --- --- --- --- --- --- --- --- ---
             713         722         731         740         749         758
   GCA GCG CTT TTG GAT GAT TGC ATA TTC AAC ATG GTT CTC TTG AAG GTG CCT TCT
   --- --- --- --- --- --- --- --- --- --- --- --- --- --- --- --- --- ---
                                             M   V   L   L   K   V   P   S 767         776         785         794         803         812
   TCA CTA AGT GCC GAG GAG CTG GAA GCC ATC AAG TTA ATT AGA TTT GGC AAA AAG
   --- --- --- --- --- --- --- --- --- --- --- --- --- --- --- --- --- ---
    S   L   S   A   E   E   L   E   A   I   K   L   I   R   F   G   K   K 821         830         839         848         857         866
   AAA AAT ACA CAT TCA CTG TTT GTT TTT ATA ATC CCT GAA AAT TTT AAA GGT TGT
   --- --- --- --- --- --- --- --- --- --- --- --- --- --- --- --- --- ---
    K   N   T   H   S   L   F   V   F   I   I   P   E   N   F   K   G   C 875         884         893         902         911         920
   ATT TCA GGG CAT GGA ATG GAT ATT GCT TTA ACT GAA CCA CTG ACA ATG GAA AAA
   --- --- --- --- --- --- --- --- --- --- --- --- --- --- --- --- --- ---
    I   S   G   H   G   M   D   I   A   L   T   E   P   L   T   M   E   K 929         938         947         956         965         974
   ATG AGT AAT GTG GTA AAA TAC TGG ACA ACA TGT CCC TCA AAC ACT GTT AAG ACT
   --- --- --- --- --- --- --- --- --- --- --- --- --- --- --- --- --- ---
    M   S   N   V   V   K   Y   W   T   T   C   P   S   N   T   V   K   T
```

FIG. 2A

```
          1685         1694         1703         1712         1721         1730
ACA AAT CAG AAC ATT TCA ATT CAT TTA CCT TCA GCC ATG CCC CCG GTC TCA AGC
--- --- --- --- --- --- --- --- --- --- --- --- --- --- --- --- --- ---
 T   N   Q   N   I   S   I   H   L   P   S   A   M   P   P   V   S   S 1739         1748         1757         1766         1775         1784
TTC TCC CTC GGC ACT GCA CTT CTG GGT TGG GCC AGA CGT GCA CTA CAC ATC CCA
--- --- --- --- --- --- --- --- --- --- --- --- --- --- --- --- --- ---
 F   S   L   G   T   A   L   L   G   W   A   R   R   A   L   H   I   P 1793         1802         1811         1820         1829         1838
ACT GTC TGC AAC AGT TTT GGG CGT ATT AAA AGC ACA TGT TTG AAA TTC ACA CTC
--- --- --- --- --- --- --- --- --- --- --- --- --- --- --- --- --- ---
 T   V   C   N   S   F   G   R   I   K   S   T   C   L   K   F   T   L 1847         1856         1865         1874         1883         1892
TCA ACC ACC TAC TGG GCG CAG TTT GAC AAT CTA GGA AAA GTG GAA CAA AGA ATG
--- --- --- --- --- --- --- --- --- --- --- --- --- --- --- --- --- ---
 S   T   T   Y   W   A   Q   F   D   N   L   G   K   V   E   Q   R   M 1901         1910         1919         1928         1937         1946
ATT TTG AAA GCT CCA CCC AAA GAC CTA ATA TCA AAA GAG TTG GCA TGG TTT GGC
--- --- --- --- --- --- --- --- --- --- --- --- --- --- --- --- --- ---
 I   L   K   A   P   P   K   D   L   I   S   K   E   L   A   W   F   G 1955         1964         1973         1982         1991         2000
TTC TGA TAA ATG CAC TCA AAG CTT CTG CAG ATA GAA AGA CCA GCA GCG AAA AAG
--- --- --- --- --- --- --- --- --- --- --- --- --- --- --- --- --- ---
 F   *   *

2009         2018         2027         2036         2045         2054
CTG GCC ACA CAC TGT CAC TCA TCT TCA TAC ACA CTT GGA TCC CCG CCA GCC AGA
--- --- --- --- --- --- --- --- --- --- --- --- --- --- --- --- --- ---

2063         2072         2081         2090         2099         2108
GAG CTA CAA GAA CAA ATG GCC TCA GTG ACC TAC ACT CTC TTT TCT CAA AAA ATA
--- --- --- --- --- --- --- --- --- --- --- --- --- --- --- --- --- ---

2117         2126
TTC CAC AAT TTA TGA AAA AAA A 3'
--- --- --- --- --- --- --- -
```

FIG. 2C

Homology with Max (rat)

gnl|PID|d1003848 (D14448) Max [Rattus norvegicus]
          Length = 151

Score = 93 (42.1 bits), Expect = 0.00037, P = 0.00037
 Identities = 17/50 (34%), Positives = 30/50 (60%)

22P4G9:     5 HSSKEKLRRERIKYCCEQLRTLLPYVKGRKNDAASVLEATVDYVKYIREK 54
              H++ E+ RR+ IK    LR  +P ++G K   A +L+    +Y++Y+R K
Max:       19 HNALERKRRDHIKDSFHSLRDSVPSLQGEKASRAQILDKATEYIQYMRRK 68

Homology with Mxi (zebrafish)

sp|P50541|MXI1_BRARE MAX INTERACTING PROTEIN 1 (MXI1 PROTEIN)
gi|505977
          (U10638) zMxi1 [Brachydanio rerio]
          Length = 243

Score = 64 (29.0 bits), Expect = 3.3, P = 0.96
 Identities = 11/24 (45%), Positives = 17/24 (70%)

22P4G9:     5 HSSKEKLRRERIKYCCEQLRTLLP 28
              H+  EK RR  ++ C E+L+TL+P
Mxi:       81 HNELEKNRRAHLRLCLERLKTLIP 104

FIG. 3

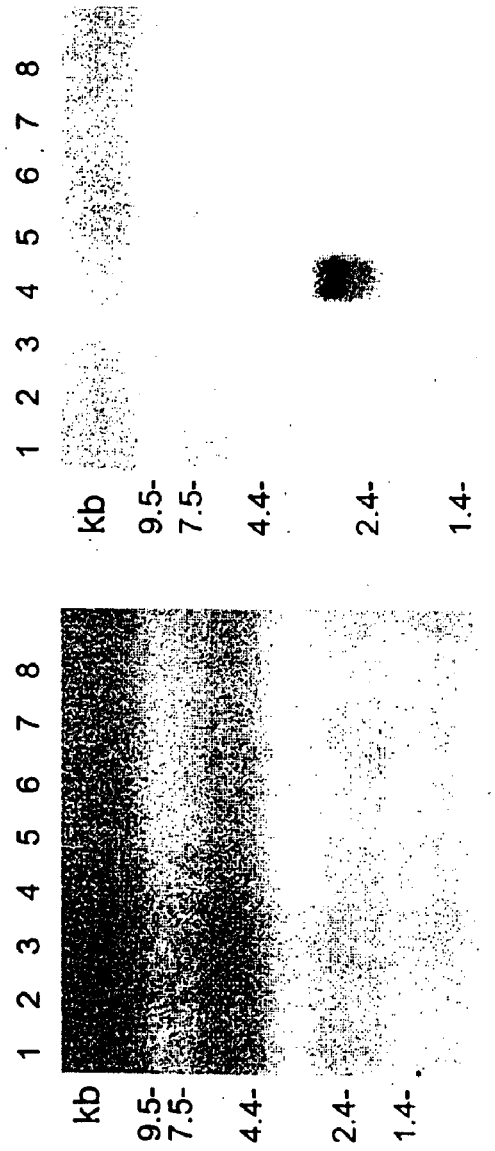

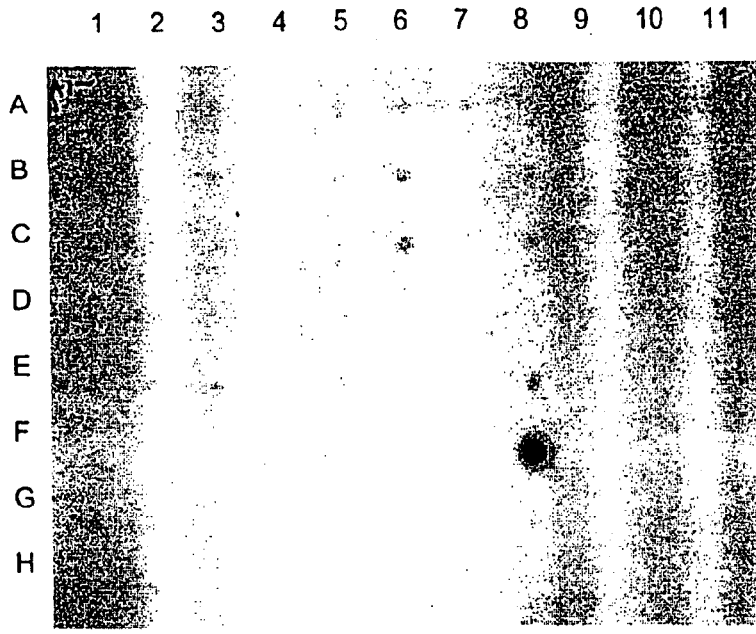

| | | | |
|---|---|---|---|
| A1 whole brain | B1 cerebral cortex | C1 frontal lobe | D1 parietal lobe |
| A2 cerebellum, left | B2 cerebellum, right | C2 corpus callosum | D2 amygdala |
| A3 substantia nigra | B3 accumbens nucleus | C3 thalamus | D3 pituitary gland |
| A4 heart | B4 aorta | C4 atrium, left | D4 atrium, right |
| A5 esophagus | B5 stomach | C5 duodenum | D5 jejunum |
| A6 colon, transverse | B6 colon, descending | C6 rectum | D6 - |
| A7 kidney | B7 skeletal muscle | C7 spleen | D7 thymus |
| A8 lung | B8 placenta | C8 bladder | D8 uterus |
| A9 liver | B9 pancreas | C9 adrenal gland | D9 thyroid gland |
| A10 HL60, leukemia | B10 HeLa, S3 | C10 K562, leukemia | D10 MOLT-4, leukemia |
| A11 fetal brain | B11 fetal heart | C11 fetal kidney | D11 fetal liver |

| | | | |
|---|---|---|---|
| E1 occipital lobe | F1 temporal lobe | G1 paracentral gyrus | H1 pons |
| E2 caudate nucleus | F2 hippocampus | G2 medulla oblongata | H2 putamen |
| E3 spinal cord | F3 - | G3 - | H3 - |
| E4 ventricle, left | F4 ventricle, right | G4 interventricular septum | H4 apex of the heart |
| E5 ileum | F5 ilocecum | G5 appendix | H5 colon, ascending |
| E6 - | F6 | G6 - | H6 - |
| E7 leukocytes | F7 lymph node | G7 bone marrow | H7 trachea |
| E8 prostate | F8 testis | G8 ovary | H8 - |
| E9 salivary gland | F9 mammary gland | G9 - | H9 - |
| E10 RAJI, lymphoma | F10 DAUDI, lymphoma | G10 SW480, colon cancer | H10 A549, lung cancer |
| E11 fetal spleen | F11 fetal thymus | G11 fetal lung | H11 - |

Panels:

A
1. Brain
2. Prostate
3. LAPC-4 AD
4. LAPC-4 AI
5. LAPC-9 AD
6. HeLa
7. Murine cDNA
8. Neg. control

B
1. Brain
2. Heart
3. Kidney
4. Liver
5. Lung
6. Pancreas
7. Placenta
8. Skeletal Muscle

C
1. Colon
2. Ovary
3. Leukocytes
4. Prostate
5. Small Intestine
6. Spleen
7. Testis
8. Thymus

Lanes:

1. 293T cells transfected with pcDNA3.1
2. 293T cells transfected with PHELIX-mycHis

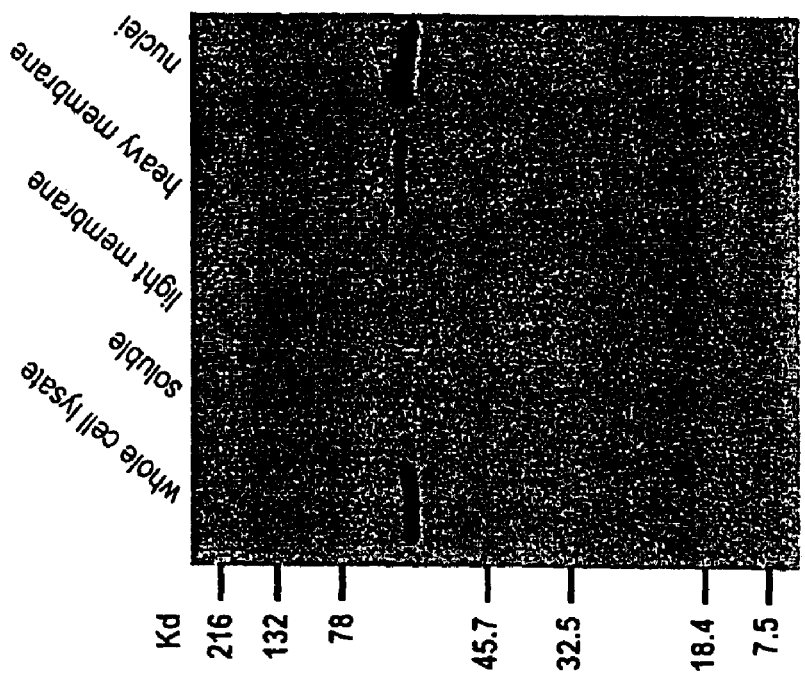
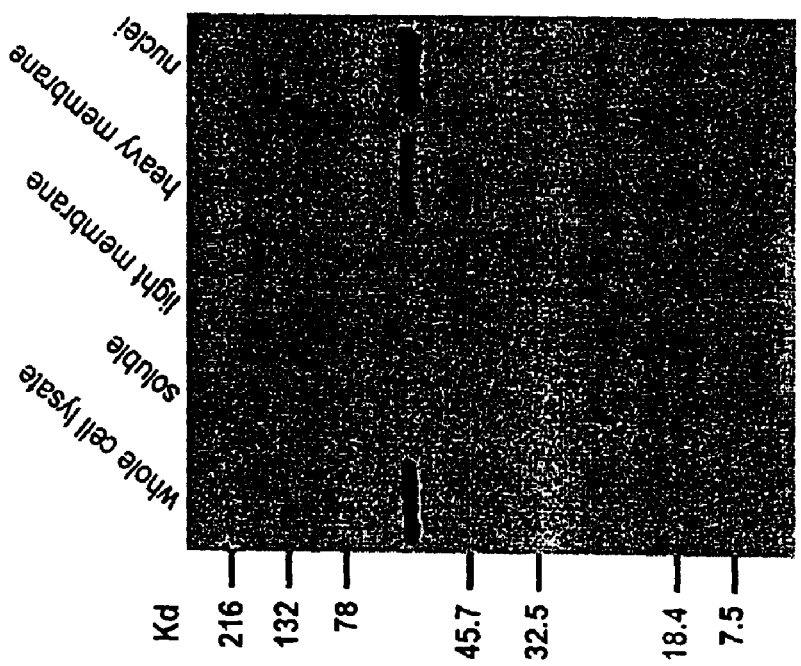
FIG. 9

SEQUENCE LISTING

<160> NUMBER OF SEQ ID NOS: 16

<210> SEQ ID NO 1
<211> LENGTH: 2128
<212> TYPE: DNA
<213> ORGANISM: Homo sapiens

<400> SEQUENCE: 1

| | | | | | |
|---|---|---|---|---|---:|
| gaccgggggg | cggttggggt | tcaccgcctc | gtgccgtact | ggcttctggg | tggcccttaa | 60 |
| tgtcttgtgc | tctaaggtgc | tgaggggaaa | gacgcgggag | gtctctggcc | tgacactatg | 120 |
| aaggaagaga | gaaactacaa | cttcgacggt | gtgagcacca | accgcctgaa | acagcagttg | 180 |
| ctggaagaag | tccgcaagaa | gtagtgaatg | gaaaacccgt | tatgagacac | aacttgaatt | 240 |
| aaatgatgaa | ctagaaaagc | aaattgttta | tctcaaggag | aaagtggaaa | aatccatgg | 300 |
| aaactcttca | gatagactat | cttctattcg | tgtctatgaa | cgaatgccag | tggaatcctt | 360 |
| aaacacatta | cttaaacagc | tagaagaaga | aagaagact | cttgaaagtc | aagtgaaata | 420 |
| ctatgcactt | aaactggaac | aagaatcaaa | ggcttaccag | aagatcaaca | atgaacgccg | 480 |
| tacataccta | gctgaaatgt | ctcagggttc | tggtttacat | caagtttcta | aaaggcaaca | 540 |
| ggtggatcaa | ctgcctagga | tgcaagagaa | tctagtgaaa | acgcaaaaat | agacatctta | 600 |
| ttagttggag | atgtcactgt | gggctacctg | gctgatactg | tacagaaact | atttgcaaac | 660 |
| atagcagaag | tcaccatcac | catcagtgac | acgaaggagg | cagcagcgct | tttggatgat | 720 |
| tgcatattca | acatggttct | cttgaaggtg | ccttcttcac | taagtgccga | ggagctggaa | 780 |
| gccatcaagt | taattagatt | tggcaaaaag | aaaaatacac | attcactgtt | tgtttttata | 840 |
| atccctgaaa | attttaaagg | ttgtatttca | gggcatggaa | tggatattgc | tttaactgaa | 900 |
| ccactgacaa | tggaaaaaat | gagtaatgtg | gtaaaatact | ggacaacatg | tccctcaaac | 960 |
| actgttaaga | ctgaaaacgc | aactgggcct | gaagaacttg | gattgcccct | gcagaggtcc | 1020 |
| tacagcgaac | acctgggata | ttttcctact | gatctatttg | cctgctctga | atctttaagg | 1080 |
| aatggcaatg | ggcttgaatt | aaatgcttcg | ttgtcagagt | tcgagaaaaa | caaaaagatc | 1140 |
| tctcttcttc | attcaagcaa | ggaaaaacta | agaagggaaa | gaatcaaaata | ttgctgtgag | 1200 |
| cagctgcgta | ctctcttgcc | gtatgtaaaa | gggagaaaga | atgatgcggc | ttcagttctt | 1260 |
| gaggcaacag | ttgattatgt | gaaatatatc | cgggagaaaa | tctctccagc | cgttatggcc | 1320 |
| cagattacag | aagcacttca | gagcaacatg | aggttttgta | agaaacaaca | acacccatt | 1380 |
| gagctgtctc | tcccaggcac | tgtcatggca | cagcgggaaa | acagtgtgat | gagcacttac | 1440 |
| tcccctgaga | gagggctcca | attcctgact | aatacgtgct | ggaatgggtg | ctccactcct | 1500 |
| gatgcagaga | gctccttgga | tgaagctgtg | agagttccat | caagctccgc | ctcagagaat | 1560 |
| gctattggtg | atccatataa | aactcacatt | tccagtgcag | cgctgtctct | gaattccttg | 1620 |
| catactgtca | gatattattc | taaagtcacc | ccttcctacg | atgcaactgc | tgtaacaaat | 1680 |
| cagaacattt | caattcattt | accttcagcc | atgcccccgg | tctcaagctt | ctccctcggc | 1740 |
| actgcacttc | tgggttgggc | cagacgtgca | ctacacatcc | caactgtctg | caacagtttt | 1800 |
| gggcgtatta | aaagcacatg | tttgaaattc | acactctcaa | ccacctactg | ggcgcagttt | 1860 |
| gacaatctag | aaaagtggga | acaaagaatg | attttgaaag | ctccacccaa | agacctaata | 1920 |
| tcaaaagagt | tggcatggtt | tggcttctga | taaatgcact | caaagcttct | gcagatagaa | 1980 |
| agaccagcag | cgaaaaagct | ggccacacac | tgtcactcat | cttcatacac | acttggatcc | 2040 |

```
ccgccagcca gagagctaca agaacaaatg gcctcagtga cctacactct ctttctctcaa    2100 aaaatattcc acaatttatg aaaaaaaa                                        2128
```

<210> SEQ ID NO 2
<211> LENGTH: 405
<212> TYPE: PRT
<213> ORGANISM: Homo sapiens

<400> SEQUENCE: 2

```
Met Val Leu Leu Lys Val Pro Ser Ser Leu Ser Ala Glu Glu Leu Glu
 1               5                  10                  15

Ala Ile Lys Leu Ile Arg Phe Gly Lys Lys Asn Thr His Ser Leu
                20                  25                  30

Phe Val Phe Ile Ile Pro Glu Asn Phe Lys Gly Cys Ile Ser Gly His
             35                  40                  45

Gly Met Asp Ile Ala Leu Thr Glu Pro Leu Thr Met Glu Lys Met Ser
 50                  55                  60

Asn Val Val Lys Tyr Trp Thr Thr Cys Pro Ser Asn Thr Val Lys Thr
65                  70                  75                  80

Glu Asn Ala Thr Gly Pro Glu Glu Leu Gly Leu Pro Leu Gln Arg Ser
                85                  90                  95

Tyr Ser Glu His Leu Gly Tyr Phe Pro Thr Asp Leu Phe Ala Cys Ser
            100                 105                 110

Glu Ser Leu Arg Asn Gly Asn Gly Leu Glu Leu Asn Ala Ser Leu Ser
        115                 120                 125

Glu Phe Glu Lys Asn Lys Lys Ile Ser Leu Leu His Ser Ser Lys Glu
    130                 135                 140

Lys Leu Arg Arg Glu Arg Ile Lys Tyr Cys Cys Glu Gln Leu Arg Thr
145                 150                 155                 160

Leu Leu Pro Tyr Val Lys Gly Arg Lys Asn Asp Ala Ala Ser Val Leu
                165                 170                 175

Glu Ala Thr Val Asp Tyr Val Lys Tyr Ile Arg Glu Lys Ile Ser Pro
            180                 185                 190

Ala Val Met Ala Gln Ile Thr Glu Ala Leu Gln Ser Asn Met Arg Phe
        195                 200                 205

Cys Lys Lys Gln Gln Thr Pro Ile Glu Leu Ser Leu Pro Gly Thr Val
    210                 215                 220

Met Ala Gln Arg Glu Asn Ser Val Met Ser Thr Tyr Ser Pro Glu Arg
225                 230                 235                 240

Gly Leu Gln Phe Leu Thr Asn Thr Cys Trp Asn Gly Cys Ser Thr Pro
                245                 250                 255

Asp Ala Glu Ser Ser Leu Asp Glu Ala Val Arg Val Pro Ser Ser Ser
            260                 265                 270

Ala Ser Glu Asn Ala Ile Gly Asp Pro Tyr Lys Thr His Ile Ser Ser
        275                 280                 285

Ala Ala Leu Ser Leu Asn Ser Leu His Thr Val Arg Tyr Tyr Ser Lys
    290                 295                 300

Val Thr Pro Ser Tyr Asp Ala Thr Val Thr Asn Gln Asn Ile Ser
305                 310                 315                 320

Ile His Leu Pro Ser Ala Met Pro Pro Val Ser Ser Phe Ser Leu Gly
                325                 330                 335

Thr Ala Leu Leu Gly Trp Ala Arg Arg Ala Leu His Ile Pro Thr Val
            340                 345                 350
```

```
Cys Asn Ser Phe Gly Arg Ile Lys Ser Thr Cys Leu Lys Phe Thr Leu
        355                 360                 365

Ser Thr Thr Tyr Trp Ala Gln Phe Asp Asn Leu Gly Lys Val Glu Gln
    370                 375                 380

Arg Met Ile Leu Lys Ala Pro Pro Lys Asp Leu Ile Ser Lys Glu Leu
385                 390                 395                 400

Ala Trp Phe Gly Phe
            405

<210> SEQ ID NO 3
<211> LENGTH: 50
<212> TYPE: PRT
<213> ORGANISM: Rattus norvegicus

<400> SEQUENCE: 3

His Asn Ala Leu Glu Arg Lys Arg Arg Asp His Ile Lys Asp Ser Phe
 1               5                  10                  15

His Ser Leu Arg Asp Ser Val Pro Ser Leu Gln Gly Glu Lys Ala Ser
            20                  25                  30

Arg Ala Gln Ile Leu Asp Lys Ala Thr Glu Tyr Ile Gln Tyr Met Arg
        35                  40                  45

Arg Lys
    50

<210> SEQ ID NO 4
<211> LENGTH: 24
<212> TYPE: PRT
<213> ORGANISM: Brachydanio rerio

<400> SEQUENCE: 4

His Asn Glu Leu Glu Lys Asn Arg Arg Ala His Leu Arg Leu Cys Leu
 1               5                  10                  15

Glu Arg Leu Lys Thr Leu Ile Pro
            20

<210> SEQ ID NO 5
<211> LENGTH: 14
<212> TYPE: DNA
<213> ORGANISM: Artificial Sequence
<220> FEATURE:
<223> OTHER INFORMATION: Primer

<400> SEQUENCE: 5
ttttgatcaa gctt                                                        14

<210> SEQ ID NO 6
<211> LENGTH: 42
<212> TYPE: DNA
<213> ORGANISM: Artificial Sequence
<220> FEATURE:
<223> OTHER INFORMATION: DNA Adaptor 1

<400> SEQUENCE: 6
ctaatacgac tcactatagg gctcgagcgg ccgcccgggc ag                          42

<210> SEQ ID NO 7
<211> LENGTH: 40
<212> TYPE: DNA
<213> ORGANISM: Artificial Sequence
<220> FEATURE:
<223> OTHER INFORMATION: DNA Adaptor 2

<400> SEQUENCE: 7
```

```
gtaatacgac tcactatagg gcagcgtggt cgcggccgag                                    40

<210> SEQ ID NO 8
<211> LENGTH: 22
<212> TYPE: DNA
<213> ORGANISM: Artificial Sequence
<220> FEATURE:
<223> OTHER INFORMATION: PCR Primer 1

<400> SEQUENCE: 8
ctaatacgac tcactatagg gc                                                      22

<210> SEQ ID NO 9
<211> LENGTH: 22
<212> TYPE: DNA
<213> ORGANISM: Artificial Sequence
<220> FEATURE:
<223> OTHER INFORMATION: Nested primer (NP)1

<400> SEQUENCE: 9
tcgagcggcc gcccgggcag ga                                                      22

<210> SEQ ID NO 10
<211> LENGTH: 20
<212> TYPE: DNA
<213> ORGANISM: Artificial Sequence
<220> FEATURE:
<223> OTHER INFORMATION: Nested primer (NP)2

<400> SEQUENCE: 10
agcgtggtcg cggccgagga                                                         20

<210> SEQ ID NO 11
<211> LENGTH: 23
<212> TYPE: DNA
<213> ORGANISM: Artificial Sequence
<220> FEATURE:
<223> OTHER INFORMATION: RT-PCR primer 22P4G9.1

<400> SEQUENCE: 11
ctgcgtactc tcttgccgta tgt                                                     23

<210> SEQ ID NO 12
<211> LENGTH: 24
<212> TYPE: DNA
<213> ORGANISM: Artificial Sequence
<220> FEATURE:
<223> OTHER INFORMATION: RT-PCR primer 22P4G9.2

<400> SEQUENCE: 12
gctcaatggg tgtttgttgt ttct                                                    24

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
atatcgccgc gctcgtcgtc gacaa                                                   25

<210> SEQ ID NO 14
<211> LENGTH: 26
<212> TYPE: DNA
```

-continued

```
<213> ORGANISM: Artificial Sequence
<220> FEATURE:
<223> OTHER INFORMATION: Primer

<400> SEQUENCE: 14
agccacacgc agctcattgt agaagg                                              26

<210> SEQ ID NO 15
<211> LENGTH: 12
<212> TYPE: DNA
<213> ORGANISM: Artificial Sequence
<220> FEATURE:
<223> OTHER INFORMATION: Primer

<400> SEQUENCE: 15
gatcctgccc gg                                                             12

<210> SEQ ID NO 16
<211> LENGTH: 10
<212> TYPE: DNA
<213> ORGANISM: Artificial Sequence
<220> FEATURE:
<223> OTHER INFORMATION: Primer

<400> SEQUENCE: 16
gatcctcggc                                                                10
```

PHELIX: A TESTIS-SPECIFIC PROTEIN EXPRESSED IN CANCER

This application claims the benefit of U.S. provisional patent applications No. 60/106,524, filed Oct. 31, 1998, now abandoned, and No. 60/098,610, filed Aug. 31, 1998, the entire contents of each of which are incorporated herein by reference.

FIELD OF THE INVENTION

The invention described herein relates to a novel gene and its encoded protein, termed PHELIX, and to diagnostic and therapeutic methods and compositions useful in the management of various cancers which express PHELIX, particularly including prostate, bladder, testicular, and ovarian cancer.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Generally speaking, the fundamental problem in the management of the deadliest cancers is the lack of effective and non-toxic systemic therapies. Molecular medicine promises to redefine the ways in which these cancers are managed. Unquestionably, there is an intensive worldwide effort aimed at the development of novel molecular approaches to cancer diagnosis and treatment. For example, there is a great interest in identifying truly tumor-specific genes and proteins that could be used as diagnostic and prognostic markers and/or therapeutic targets or agents. Research efforts in these areas are encouraging, and the increasing availability of useful molecular technologies has accelerated the acquisition of meaningful knowledge about cancer. Nevertheless, progress is slow and generally uneven.

As discussed below, the management of prostate cancer serves as a good example of the limited extent to which molecular biology has translated into real progress in the clinic. With limited exceptions, the situation is more or less the same for the other major carcinomas mentioned above.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease— second only to lung cancer. Despite the magnitude of these figures, there is still no effective treatment for metastatic prostate cancer. Surgical prostatectomy, radiation therapy, hormone ablation therapy, and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects.

Most prostate cancers initially occur in the peripheral zone of the prostate gland, away from the urethra. Tumors within this zone may not produce any symptoms and, as a result, most men with early-stage prostate cancer will not present clinical symptoms of the disease until significant progression has occurred. Tumor progression into the transition zone of the prostate may lead to urethral obstruction, thus producing the first symptoms of the disease. However, these clinical symptoms are indistinguishable from the common non-malignant condition of benign prostatic hyperplasia (BPH). Early detection and diagnosis of prostate cancer currently relies on digital rectal examinations (DRE), prostate specific antigen (PSA) measurements, transrectal ultrasonography (TRUS), and transrectal needle biopsy (TRNB). At present, serum PSA measurement in combination with DRE represent the leading tool used to detect and diagnose prostate cancer. Both have major limitations which have fueled intensive research into finding better diagnostic markers of this disease.

Similarly, there is no available marker that can predict the emergence of the typically fatal metastatic stage of prostate cancer. Diagnosis of metastatic stage is presently achieved by open surgical or laparoscopic pelvic lymphadenectomy, whole body radionuclide scans, skeletal radiography, and/or bone lesion biopsy analysis. Clearly, better imaging and other less invasive diagnostic methods offer the promise of easing the difficulty those procedures place on a patient, as well as improving diagnostic accuracy and opening therapeutic options. A similar problem is the lack of an effective prognostic marker for determining which cancers are indolent and which ones are or will be aggressive. PSA, for example, fails to discriminate accurately between indolent and aggressive cancers. Until there are prostate tumor markers capable of reliably identifying early-stage disease, predicting susceptibility to metastasis, and precisely imaging tumors, the management of prostate cancer will continue to be extremely difficult.

PSA is the most widely used tumor marker for screening, diagnosis, and monitoring prostate cancer today. In particular, several immunoassays for the detection of serum PSA are in widespread clinical use. Recently, a reverse transcriptase-polymerase chain reaction (RT-PCR) assay for PSA mRNA in serum has been developed. However, PSA is not a disease-specific marker, as elevated levels of PSA are detectable in a large percentage of patients with BPH and prostatitis (25–86%)(Gao et al., 1997, Prostate 31: 264–281), as well as in other nonmalignant disorders and in some normal men, a factor which significantly limits the diagnostic specificity of this marker. For example, elevations in serum PSA of between 4 to 10 ng/ml are observed in BPH, and even higher values are observed in prostatitis, particularly acute prostatis. BPH is an extremely common condition in men. Further confusing the situation is the fact that serum PSA elevations may be observed without any indication of disease from DRE, and visa-versa. Moreover, it is now recognized that PSA is not prostate-specific (Gao et al., supra, for review).

Various methods designed to improve the specificity of PSA-based detection have been described, such as measuring PSA density and the ratio of free vs. complexed PSA. However, none of these methodologies have been able to reproducibly distinguish benign from malignant prostate disease. In addition, PSA diagnostics have sensitivities of between 57–79% (Cupp & Osterling, 1993, Mayo Clin Proc 68:297–306), and thus miss identifying prostate cancer in a significant population of men with the disease.

There are some known markers which are expressed predominantly in prostate, such as prostate specific membrane antigen (PSM), a hydrolase with 85% identity to a rat neuropeptidase (Carter et al., 1996, Proc. Natl. Acad. Sci. USA 93: 749; Bzdega et al., 1997, J. Neurochem. 69:2270). However, the expression of PSM in small intestine and brain (Israeli et al., 1994, Cancer Res. 54: 1807), as well its potential role in neuropeptide catabolism in brain, raises concern of potential neurotoxicity with anti-PSM therapies. Preliminary results using an Indium-111 labeled, anti-PSM monoclonal antibody to image recurrent prostate cancer show some promise (Sodee et al., 1996, Clin Nuc Med 21: 759–766). More recently identified prostate cancer markers include PCTA-1 (Su et al., 1996, Proc. Natl. Acad. Sci. USA 93: 7252) and prostate stem cell antigen (PSCA) (Reiter et al., 1998, Proc. Natl. Acad. Sci. USA 95: 1735). PCTA-1, a novel galectin, is largely secreted into the media of expressing cells and may hold promise as a diagnostic serum marker for prostate cancer (Su et al., 1996). PSCA, a GPI-linked cell surface molecule, was cloned from LAPC-4 cDNA and is unique in that it is expressed primarily in basal cells of normal prostate tissue and in cancer epithelia (Reiter et al., 1998). Vaccines for prostate cancer are also being actively explored with a variety of antigens, including PSM and PSA.

SUMMARY OF THE INVENTION

The present invention relates to a novel gene and protein designated PHELIX. In normal individuals, PHELIX is expressed only in testis. However, PHELIX is expressed at high levels in advanced and metastatic prostate cancer, and is also expressed at lower levels in other types of human cancers, including testicular, bladder and ovarian cancers. The PHELIX expression pattern is reminiscent of the Cancer-Testis (CT) antigens or MAGEs, which are testis-specific genes that are up-regulated in melanomas and other cancers (Van den Eynde and Boon, Int J Clin Lab Res. 27:81–86, 1997). Due to their tissue-specific expression and high expression levels in cancer, the MAGEs are currently being investigated as targets for cancer vaccines (Durrant, Anticancer Drugs 8:727–733, 1997; Reynolds et al., Int J Cancer 72:972–976, 1997). The expression pattern of PHELIX suggests that it is likewise an ideal target for a cancer vaccine approach to prostate cancer, particularly in view of the testis-specific expression pattern of the PHELIX gene in normal human tissues.

The structure of the PHELIX protein includes a basic helix-loop-helix (bHLH) domain of approximately 50 amino acids bearing some homology to the transcription factors Myc, Max and Mxi-1. In addition, the PHELIX protein appears to be nuclear, as its primary structure contains 2 potential nuclear localization sequences and analysis of subcellular fractions of PHELIX-expressing cells localize the protein predominantly to the nucleus. Accordingly, PHELIX may encode a novel transcription factor that normally exhibits a testis-specific expression pattern but is turned on in prostate cancer as well as in other cancers. Its structural features as a potential transcription factor also suggest that PHELIX may be a small molecule target. In addition, PHELIX may also be useful as a diagnostic, staging and/or prognostic marker.

Although the precise function of PHELIX is presently unknown, its homology with other bHLH transcription factors implies a similar function which may include interaction with other bHLH proteins. Aberrant expression of PHELIX in cancer may result in modulated transcription of genes involved in the development and/or progression of prostate cancer and other cancers expressing PHELIX. A number of potential approaches to the treatment of cancers expressing PHELIX involving the inhibition of PHELIX function are therefore possible.

The invention provides polynucleotides corresponding or complementary to all or part of the PHELIX genes, mRNAs, and/or coding sequences, preferably in isolated form, including polynucleotides encoding PHELIX proteins and fragments thereof, DNA, RNA, DNA/RNA hybrid, and related molecules, polynucleotides or oligonucleotides complementary to the PHELIX genes or mRNA sequences or parts thereof, and polynucleotides or oligonucleotides which hybridize to the PHELIX genes, mRNAs, or to PHELIX-encoding polynucleotides. Also provided are means for isolating cDNAs and the genes encoding PHELIX. Recombinant DNA molecules containing PHELIX polynucleotides, cells transformed or transduced with such molecules, and host-vector systems for the expression of PHELIX gene products are also provided. The invention further provides PHELIX proteins and polypeptide fragments thereof. The invention further provides antibodies that bind to PHELIX proteins and polypeptide fragments thereof, including polyclonal and monoclonal antibodies, murine and other mammalian antibodies, chimeric antibodies, humanized and fully human antibodies, antibodies labeled with a detectable marker. The invention further provides methods for detecting the presence of PHELIX polynucleotides and proteins in various biological samples, as well as methods for identifying cells that express PHELIX. The invention further provides various therapeutic compositions and strategies for treating cancers which express PHELIX such as prostate, bladder, ovarian and testicular cancers, including therapies aimed at inhibiting the transcription, translation, processing or function of PHELIX and cancer vaccines.

BRIEF DESCRIPTION OF THE FIGURES

FIG. 3. Amino acid sequence alignment of human PHELIX with the bHLH domains of the transcription factors Max and Mxi, (SEQ ID NO: 3 and SEQ ID NO: 4, respectively), showing a 60% similarity to Max over a 50 amino acid region, and a 70% similarity to Mxi over a 24 amino acid region.

FIG. 4. Northern blot analysis of PHELIX expression in various normal human tissues showing exclusive expression in testis.

FIG. 5. An mRNA dot blot analysis of PHELIX expression in 76 different samples from human tissues showing exclusive expression in testis.

FIG. 9. Western blot analysis of subcellular fractions of PHELIX expressing 293T cells, showing localization predominantly in the nuclear fraction of cells. Left: Blot probed with 0.1 µg/ml of anti-His Ab. Right: Blot probed with 1 µg/ml of affinity purified anti-PHELIX polyclonal Ab.

DETAILED DESCRIPTION OF THE INVENTION

Figure 1:
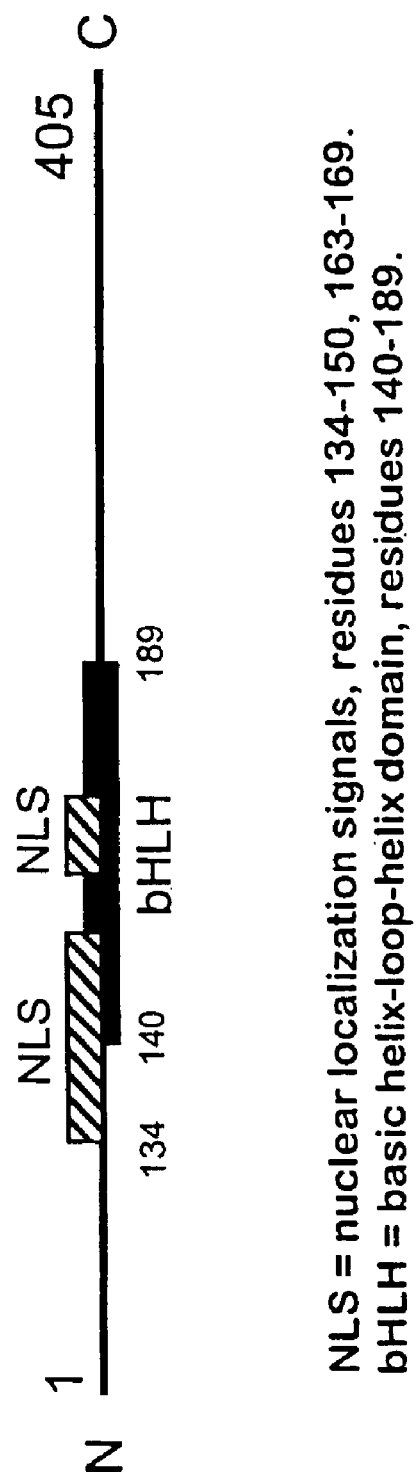
FIG. 1. Schematic representation of the human PHELIX protein structure. The nuclear localization signals are shown by diagonally striped bars, and the basic Helix Loop Helix (bHLH) domain is shown by the solid bar. The numbering scheme is based on the amino acid sequence of PHELIX encoded by a full length cDNA.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers which have extended through the prostate capsule, and are meant to include stage C disease under the American Urological Association (AUA) system, stage C1–C2 disease under the Whitmore-Jewett system, and stage T3–T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers which have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6XSSC/0.1% SDS/100 µg/ml ssDNA, in which temperatures for hybridization are above 37 degrees C. and temperatures for washing in 0.1XSSC/0.1% SDS are above 55 degrees C., and most preferably to stringent hybridization conditions.

In the context of amino acid sequence comparisons, the term "identity" is used to express the percentage of amino acid residues at the same relative position which are the same. Also in this context, the term "homology" is used to express the percentage of amino acid residues at the same relative positions which are either identical or are similar, using the conserved amino acid criteria of BLAST analysis, as is generally understood in the art. Further details regarding amino acid substitutions, which are considered conservative under such criteria, are provided below.

Additional definitions are provided throughout the subsections which follow.

STRUCTURE AND EXPRESSION OF PHELIX

As is further described in the Examples which follow, the PHELIX gene and protein have been characterized using a number of analytical approaches. For example, analyses of nucleotide coding and amino acid sequences were conducted in order to identify potentially related molecules, as well as recognizable structural domains, topological features, and other elements within the PHELIX mRNA and protein structure. RT-PCR, Northern blot and RNA dot blot analyses of PHELIX mRNA expression were conducted in order to establish the range of normal and cancerous tissues expressing PHELIX message. Western blot analyses were used to characterize anti-PHELIX antibody preparations and to define the subcellular localization of the PHELIX protein.

PHELIX is a basic Helix Loop Helix (bHLH) protein bearing homology to several known transcription factors in the region of the bHLH domain, including Max (Backwood and Eisenman, 1991, Science 251: 1211–1217), Mxi (Zenos et al., 1993, Cell 72: 223–232) and Myc (Rabbitts et al., 1983, Nature 306: 760–765) (FIG. 3). Basic Helix Loop Helix domains frequently occur in nuclear transcription factors and function as protein-protein interaction domains involved in homodimerization or heterodimerization of two bHLH proteins. A classic example of a bHLH transcription factor is Max, which can heterodimerize with either the c-Myc protooncogene to activate transcription or with Mad to repress transcription (Luscher and Larsson, Oncogene 18:2955–2966, 1999; Grandori and Eisenman, Trends Biochem Sci 22:177–181, 1997). Similarly, PHELIX may be a transcription factor that interacts with other bHLH proteins in regulating transcription.

Figure 6:
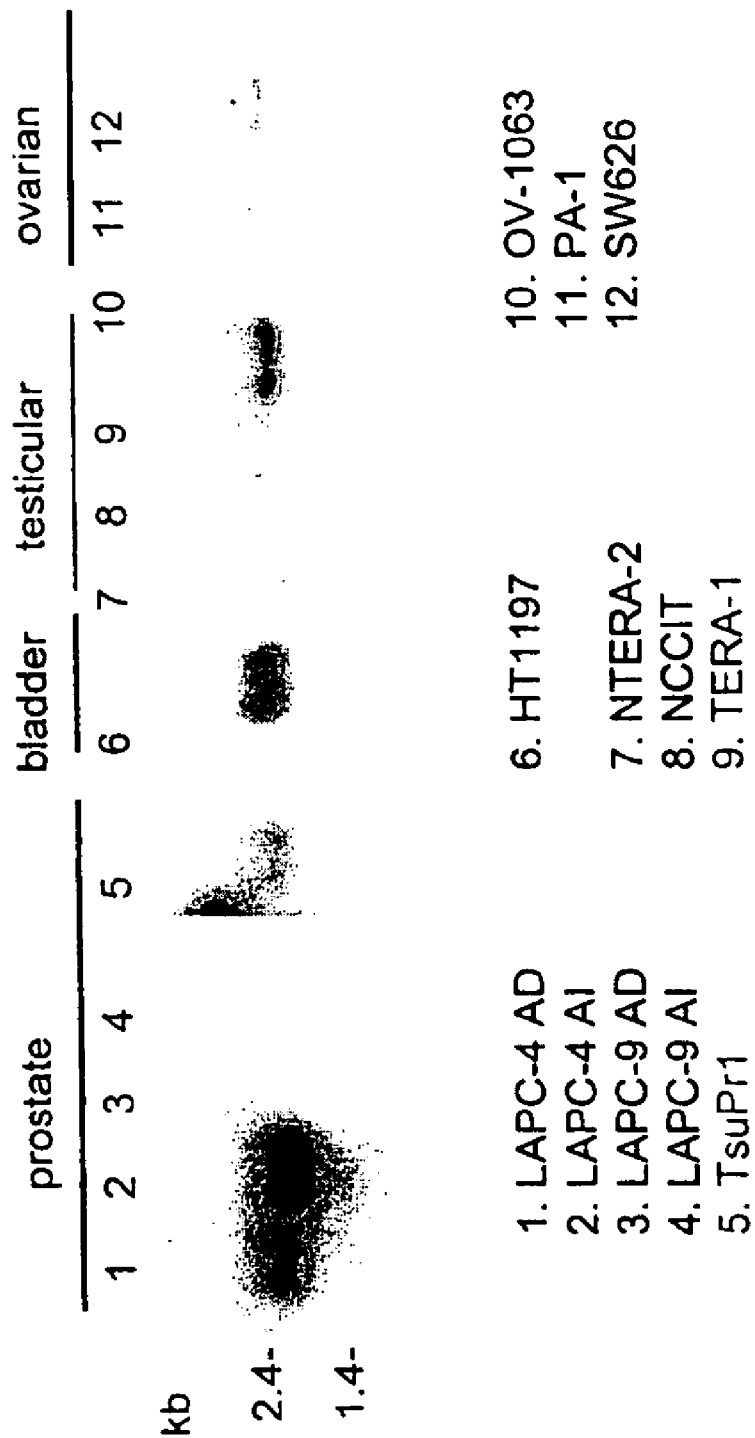
FIG. 6. Northern blot analysis showing PHELIX expression in human prostate cancer, bladder cancer, testicular cancer and ovarian cancer.
Figure 7A:
FIG. 7. Semi-quantitative RT-PCR expression analysis showing human PHELIX expression in normal testis and LAPC-4 prostate cancer xenografts.
Figure 7B:
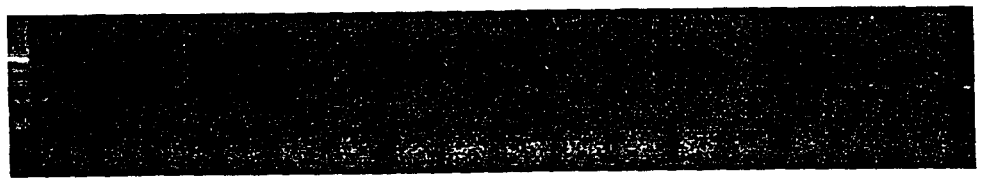
Figure 7C:

PHELIX expression is testis-specific in normal adult human tissues (FIGS. 4 and 5), but is also expressed in certain cancers, including prostate, bladder, ovarian and testicular carcinomas (FIG. 6 and 7). Human prostate tumor xenografts originally derived from a patient with high grade metastatic prostate cancer express high levels of PHELIX, with the highest levels seen in an androgen-independent xenograft (FIGS. 6 and 7). Lower level PHELIX expression is detected in several cancer cell lines derived from prostate (TsuPr1), bladder (HT1197), testis (NCCIT, TERA-1), and ovary (OV-1063, PA-1) (FIG. 6), suggesting that PHELIX is a highly testis-specific gene that may be up-regulated in various human cancers.

Figure 2B:
FIG. 2. Nucleotide and deduced amino acid sequences of human PHELIX cDNA (clone GTP1C12) (SEQ ID NO: 1 and SEQ ID NO: 2, respectively). The sequence surrounding the start ATG (AAC ATG G) exhibits a Kozak sequence (A at position −3, and G at position +1). The putative bHLH domain is underlined in bold, and two putative nuclear localization signals are boxed and shaded.

A schematic diagram of the PHELIX protein structure is shown in FIG. 1 and the cDNA sequence of the human PHELIX gene and amino acid sequence of the encoded PHELIX protein are shown in FIG. 2 (SEQ ID NO: 1 and SEQ ID NO: 2, respectively). PHELIX is a 405 amino acid protein containing a bHLH domain and two putative nuclear localization sequences (FIGS. 1 and 2). Recombinant PHELIX is expressed as a 48 kD protein in a mammalian expression system. The human PHELIX gene maps to chromosome 13$q$13.1–13.3. The PHELIX protein localizes primarily in the nucleus.

PHELIX POLYNUCLEOTIDES

One aspect of the invention provides polynucleotides corresponding or complementary to all or part of a PHELIX gene, mRNA, and/or coding sequence, preferably in isolated form, including polynucleotides encoding a PHELIX protein and fragments thereof, DNA, RNA, DNA/RNA hybrid, and related molecules, polynucleotides or oligonucleotides complementary to a PHELIX gene or mRNA sequence or a part thereof, and polynucleotides or oligonucleotides which hybridize to a PHELIX gene, mRNA, or to a PHELIX-encoding polynucleotide (collectively, "PHELIX polynucleotides"). As used herein, the PHELIX gene and protein is meant to include the PHELIX gene and protein specifically described herein and the genes and proteins corresponding to other PHELIX proteins and structurally similar variants of the foregoing. Such other PHELIX proteins and variants will generally have coding sequences which are highly homologous to the PHELIX coding sequence, and preferably will share at least about 50% amino acid identity and at least about 60% amino acid homology (using BLAST criteria), more preferably sharing 70% or greater homology (using BLAST criteria).

A PHELIX polynucleotide may comprise a polynucleotide having the nucleotide sequence of human PHELIX as shown in FIG. 2, (SEQ ID NO: 2), wherein T can also be U; a polynucleotide which encodes all or part of the PHELIX protein; a sequence complementary to the foregoing; or a polynucleotide fragment of any of the foregoing. Another embodiment comprises a polynucleotide having the sequence as shown in FIG. 2, (SEQ ID NO: 1), from nucleotide residue number 735 through nucleotide residue number 1949, wherein T can also be U. Another embodiment comprises a polynucleotide encoding a PHELIX polypeptide whose sequence is encoded by the cDNA contained in the plasmid as deposited with American Type Culture Collection as Accession No. 98956. Another embodiment comprises a polynucleotide which is capable of hybridizing under stringent hybridization conditions to the human PHELIX cDNA shown in FIG. 2, (SEQ ID NO: 1), or to a polynucleotide fragment thereof.

Specifically contemplated are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the PHELIX polynucleotides and polynucleotide sequences disclosed herein.

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemi-luminescent compound, metal chelator or enzyme. Such probes and primers can be used to detect the presence of a PHELIX polynucleotide in a sample and as a means for detecting a cell expressing a PHELIX protein. Examples of such probes include polynucleotides comprising all or part of the human PHELIX cDNA sequence shown in FIG. 2. (SEQ ID NO: 1) Examples of primer pairs capable of specifically amplifying PHELIX mRNAs are also described in the Examples which follow. As will be understood by the skilled artisan, a great many different primers and probes may be prepared based on the sequences provided in herein and used effectively to amplify and/or detect a PHELIX mRNA.

As used herein, a polynucleotide is said to be "isolated" when it is substantially separated from contaminant polynucleotides which correspond or are complementary to genes other than the PHELIX gene or which encode polypeptides other than PHELIX gene product or fragments thereof. A skilled artisan can readily employ nucleic acid isolation procedures to obtain an isolated PHELIX polynucleotide.

The PHELIX polynucleotides of the invention are useful for a variety of purposes, including but not limited to their use as probes and primers for the amplification and/or detection of the PHELIX gene(s), mRNA(s), or fragments thereof; as reagents for the diagnosis and/or prognosis of prostate cancer and other cancers; as coding sequences capable of directing the expression of PHELIX polypeptides; as tools for modulating or inhibiting the expression of the PHELIX gene(s) and/or translation of the PHELIX transcript(s); and as therapeutic agents.

METHODS FOR ISOLATING PHELIX-ENCODING NUCLEIC ACID MOLECULES

The PHELIX cDNA sequences described herein enable the isolation of other polynucleotides encoding PHELIX gene product(s), as well as the isolation of polynucleotides encoding PHELIX gene product homologues, alternatively spliced isoforms, allelic variants, and mutant forms of the PHELIX gene product. Various molecular cloning methods that can be employed to isolate full length cDNAs encoding a PHELIX gene are well known (See, for example, Sambrook, J. et al, Molecular Cloning: A Laboratory Manual, 2d edition., Cold Spring Harbor Press, N.Y., 1989; Current Protocols in Molecular Biology. Ausubel et al., Eds., Wiley and Sons, 1995). For example, lambda phage cloning methodologies may be conveniently employed, using commercially available cloning systems (e.g., Lambda ZAP Express, Stratagene). Phage clones containing PHELIX gene cDNAs may be identified by probing with a labeled PHELIX cDNA or a fragment thereof. For example, in one embodiment, the PHELIX cDNA (FIG. 2) (SEQ ID NO: 2), or a portion thereof can be synthesized and used as a probe to retrieve overlapping and full length cDNAs corresponding to a PHELIX gene. The PHELIX gene itself may be isolated by screening genomic DNA libraries, bacterial artificial chromosome libraries (BACs), yeast artificial chromosome libraries (YACs), and the like, with PHELIX DNA probes or primers.

RECOMBINANT DNA MOLECULES AND HOST-VECTOR SYSTEMS

The invention also provides recombinant DNA or RNA molecules containing a PHELIX polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a PHELIX polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such LnCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a PHELIX may be used to generate PHELIX proteins or fragments thereof using any number of host-vector systems routinely used and widely known in the art.

A wide range of host-vector systems suitable for the expression of PHELIX proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, PHELIX may be preferably expressed in several prostate cancer and non-prostate cell lines, including for example 293, 293T, rat-1, 3T3, PC-3, LNCaP and TsuPr1. The host-vector systems of the invention are useful for the production of a PHELIX protein or fragment thereof. Such host-vector systems may be employed to study the functional properties of PHELIX and PHELIX mutations.

Recombinant human PHELIX protein may be produced by mammalian cells transfected with a construct encoding PHELIX. In a particular embodiment described in the Examples, 293T cells are transfected with an expression plasmid encoding PHELIX, the PHELIX protein is expressed in the 293T cells, and the recombinant PHELIX protein is isolated using standard purification methods (e.g., affinity purification using anti-PHELIX antibodies). In another embodiment, also described in the Examples herein, the PHELIX coding sequence is subcloned into the retroviral vector pSRαMSVtkneo and used to infect various mammalian cell lines, including 3T3CL7, PC3 and LnCaP in order to establish PHELIX expressing cell lines. Various other expression systems well known in the art may also be employed. Expression constructs encoding a leader peptide joined in frame to the PHELIX coding sequence may be used for the generation of a secreted form of recombinant PHELIX protein.

Proteins encoded by the PHELIX genes, or by fragments thereof, will have a variety of uses, including but not limited to generating antibodies and in methods for identifying ligands and other agents (i.e., other bHLH proteins) and cellular constituents that bind to a PHELIX gene product. Antibodies raised against a PHELIX protein or fragment thereof may be useful in diagnostic and prognostic assays, and imaging methodologies in the management of human cancers characterized by expression of PHELIX protein, including but not limited to cancers of the prostate, bladder, ovary and testis. Such antibodies may be expressed intracellularly and used in methods of treating patients with such cancers. Various immunological assays useful for the detection of PHELIX proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting PHELIX expressing cells (e.g., in radioscintigraphic imaging methods). PHELIX proteins may also be particularly useful in generating cancer vaccines, as further described below.

PHELIX PROTEINS

Another aspect of the present invention provides PHELIX proteins and polypeptide fragments thereof. The PHELIX proteins of the invention include those specifically identified herein, as well as allelic variants, conservative substitution variants and homologs that can be isolated/generated and characterized without undue experimentation following the methods outlined below. Fusion proteins which combine parts of different PHELIX proteins or fragments thereof, as well as fusion proteins of a PHELIX protein and a heterologous polypeptide are also included. Such PHELIX proteins will be collectively referred to as the PHELIX proteins, the proteins of the invention, or PHELIX. As used herein, the term "PHELIX polypeptide" refers to a polypeptide fragment or a PHELIX protein of at least 10 amino acids, preferably at least 15 amino acids.

A specific embodiment of a PHELIX protein comprises a polypeptide having the amino acid sequence of human PHELIX as shown in FIG. 2 (SEQ ID NO: 2).

In general, naturally occurring allelic variants of human PHELIX will share a high degree of structural identity and homology (e.g., 90% or more identity). Typically, allelic variants of the PHELIX proteins will contain conservative amino acid substitutions within the PHELIX sequences described herein or will contain a substitution of an amino acid from a corresponding position in a PHELIX homologue. One class of PHELIX allelic variants will be proteins that share a high degree of homology with at least a small region of a particular PHELIX amino acid sequence, but will further contain a radical departure form the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

PHELIX proteins may be embodied in many forms, preferably in isolated form. As used herein, a protein is said to be "isolated" when physical, mechanical or chemical methods are employed to remove the PHELIX protein from cellular constituents that are normally associated with the protein. A skilled artisan can readily employ standard purification methods to obtain an isolated PHELIX protein. A purified PHELIX protein molecule will be substantially free of other proteins or molecules which impair the binding of PHELIX to antibody or other ligand. The nature and degree of isolation and purification will depend on the intended use. Embodiments of a PHELIX protein include a purified PHELIX protein and a functional, soluble PHELIX protein. In one form, such functional, soluble PHELIX proteins or fragments thereof retain the ability to bind antibody or other ligand.

The invention also provides PHELIX polypeptides comprising biologically active fragments of the PHELIX amino acid sequence, such as a polypeptide corresponding to part of the amino acid sequences for PHELIX as shown in FIG. 2 (SEQ ID NO: 2). Such polypeptides of the invention exhibit properties of the PHELIX protein, such as the ability to elicit the generation of antibodies which specifically bind an epitope associated with the PHELIX protein.

PHELIX polypeptides can be generated using standard peptide synthesis technology or using chemical cleavage methods well known in the art based on the amino acid sequences of the human PHELIX proteins disclosed herein. Alternatively, recombinant methods can be used to generate nucleic acid molecules that encode a polypeptide fragment of a PHELIX protein. In this regard, the PHELIX-encoding nucleic acid molecules described herein provide means for generating defined fragments of PHELIX proteins. PHELIX polypeptides are particularly useful in generating and characterizing domain specific antibodies (e.g., antibodies recognizing an extracellular or intracellular epitope of a PHELIX protein), in identifying agents or cellular factors that bind to PHELIX or a particular structural domain thereof, and in various therapeutic contexts, including but not limited to cancer vaccines.

PHELIX polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schult or Jameson-Wolf analysis, or on the basis of immunogenicity. Fragments containing such structures are particularly useful in generating subunit specific anti-PHELIX antibodies or in identifying cellular factors that bind to PHELIX.

In a specific embodiment described in the examples which follow, PHELIX is conveniently expressed in 293T cells transfected with a CMV-driven expression vector encoding PHELIX with a C-terminal 6XHis and MYC tag (pcDNA3.1/mycHIS, Invitrogen). The secreted HIS-tagged PHELIX in the culture media may be purified using a nickel column using standard techniques.

PHELIX ANTIBODIES

Another aspect of the invention provides antibodies that bind to PHELIX proteins and polypeptides. The most preferred antibodies will specifically bind to a PHELIX protein and will not bind (or will bind weakly) to non-PHELIX proteins and polypeptides. Anti-PHELIX antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule which binds to its target, i.e., the antigen binding region.

PHELIX antibodies of the invention may be particularly useful in prostate cancer diagnostic and prognostic assays, and imaging methodologies. Intracellularly expressed antibodies (e.g., single chain antibodies) may be therapeutically useful in treating cancers in which the expression of PHELIX is involved, such as for example advanced and metastatic prostate cancers. Similarly, such antibodies may be useful in the treatment, diagnosis, and/or prognosis of other cancers, to the extent PHELIX is also expressed or overexpressed in other types of cancer. Other cancers that expresses PHELIX include without limitation cancers of the bladder, ovary and testis.

The invention also provides various immunological assays useful for the detection and quantification of PHELIX and mutant PHELIX proteins and polypeptides. Such assays generally comprise one or more PHELIX antibodies capable of recognizing and binding a PHELIX or mutant PHELIX protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer and other cancers expressing PHELIX (e.g., cancers of the bladder, ovary and testis) are also provided by the invention, including but not limited to radioscintigraphic imaging methods using labeled PHELIX antibodies. Such assays may be clinically useful in the detection, monitoring, and prognosis of PHELIX expressing cancers such as prostate cancer.

PHELIX antibodies may also be used in methods for purifying PHELIX and mutant PHELIX proteins and polypeptides and for isolating PHELIX homologues and related molecules. For example, in one embodiment, the method of purifying a PHELIX protein comprises incubating a PHELIX antibody, which has been coupled to a solid matrix, with a lysate or other solution containing PHELIX under conditions which permit the PHELIX antibody to bind to PHELIX; washing the solid matrix to eliminate impurities; and eluting the PHELIX from the coupled antibody. Other uses of the PHELIX antibodies of the invention include generating anti-idiotypic antibodies that mimic the PHELIX protein.

Various methods for the preparation of antibodies are well known in the art. For example, antibodies may be prepared by immunizing a suitable mammalian host using a PHELIX protein, peptide, or fragment, in isolated or immunoconjugated form (Antibodies: A Laboratory Manual, CSH Press, Eds., Harlow, and Lane (1988); Harlow, Antibodies, Cold Spring Harbor Press, N.Y. (1989)). In addition, fusion proteins of PHELIX may also be used, such as a PHELIX GST-fusion protein. In a particular embodiment, a GST fusion protein comprising all or most of the open reading frame amino acid sequence of FIG. 2 (SEQ ID NO. 2) may be produced and used as an immunogen to generate appropriate antibodies. In another embodiment, a PHELIX peptide may be synthesized and used as an immunogen. As described in Example 5, below, the 15-mer PHELIX peptide HSSKEKLRRERIKYC (positions 140–154 of SEQ ID NO: 2) was conjugated to keyhole limpet hemocyanin (KLH) and used to immunize a rabbit. The resulting polyclonal antiserum specifically recognized PHELIX expressed in a recombinant mammalian expression system.

In addition, naked DNA immunization techniques known in the art may be used (with or without purified PHELIX protein or PHELIX expressing cells) to generate an immune response to the encoded immunogen (for review, see Donnelly et al., 1997, Ann. Rev. Immunol. 15:617–648).

The amino acid sequence of PHELIX as shown in FIG. 2 (SEQ ID NO: 2) may be used to select specific regions of the PHELIX protein for generating antibodies. For example, hydrophobicity and hydrophilicity analyses of the PHELIX amino acid sequence may be used to identify hydrophilic regions in the PHELIX structure. Regions of the PHELIX protein that show immunogenic structure, as well as other regions and domains, can readily be identified using various other methods known in the art, such as Chou-Fasman, Gamier-Robson, Kyte-Doolittle, Eisenberg, Karplus-Schultz or Jameson-Wolf analysis. Methods for the generation of PHELIX antibodies are further illustrated by way of the examples provided herein.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a PHELIX immunogen is conducted generally by injection over a suitable time period and with use of a suitable adjuvant, as is generally understood in the art. During the immunization schedule, titers of antibodies can be taken to determine adequacy of antibody formation.

PHELIX monoclonal antibodies are preferred and may be produced by various means well known in the art. For example, immortalized cell lines which secrete a desired monoclonal antibody may be prepared using the standard hybridoma technology of Kohler and Milstein or modifications which immortalize producing B cells, as is generally known. The immortalized cell lines secreting the desired antibodies are screened by immunoassay in which the antigen is the PHELIX protein or a PHELIX fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the PHELIX protein can also be produced in the context of chimeric or CDR grafted antibodies of multiple species origin. Humanized or human PHELIX antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522–525; Riechmnan et al., 1988, Nature 332: 323–327; Verhoeyen et al., 1988, Science 239: 1534–1536). See also, Carter et al., 1993, Proc. Natl. Acad. Sci. USA 89: 4285 and Sims et al., 1993, J. Immunol. 151: 2296. Methods for producing fully human monoclonal antibodies include phage display and transgenic methods (for review, see Vaughan et al., 1998, Nature Biotechnology 16: 535–539).

Fully human PHELIX monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human PHELIX monoclonal antibodies may also be produced using transgenic mice engineered to contain human immunoglobulin gene loci as described in PCT Patent Application WO98/24893, Kucheriapati and Jakobovits et al., published Dec. 3, 1997 (see also, Jakobovits, 1998, Exp. Opin. Invest. Drugs 7(4): 607–614). This method avoids the in vitro manipulation required with phage display technology and efficiently produces high affinity authentic human antibodies.

Reactivity of PHELIX antibodies with a PHELIX protein may be established by a number of well known means, including Western blot, immunoprecipitation, ELISA, and FACS analyses using, as appropriate, PHELIX proteins, peptides, PHELIX-expressing cells or extracts thereof.

A PHELIX antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more PHELIX epitopes may be generated using methods generally known in the art. Homodimeric antibodies may also be generated by cross-linking techniques known in the art (e.g., Wolff et al., Cancer Res. 53: 2560–2565).

METHODS FOR THE DETECTION OF PHELIX

Another aspect of the present invention relates to methods for detecting PHELIX polynucleotides and PHELIX proteins, as well as methods for identifying a cell which expresses PHELIX.

More particularly, the invention provides assays for the detection of PHELIX polynucleotides in a biological sample, such as serum, bone, prostate, and other tissues, urine, semen, cell preparations, and the like. Detectable PHELIX polynucleotides include, for example, a PHELIX gene or fragments thereof, PHELIX mRNA, alternative splice variant PHELIX mRNAs, and recombinant DNA or RNA molecules containing a PHELIX polynucleotide. A number of methods for amplifying and/or detecting the presence of PHELIX polynucleotides are well known in the art and may be employed in the practice of this aspect of the invention.

In one embodiment, a method for detecting a PHELIX mRNA in a biological sample comprises producing cDNA from the sample by reverse transcription using at least one primer; amplifying the cDNA so produced using a PHELIX polynucleotides as sense and antisense primers to amplify PHELIX cDNAs therein; and detecting the presence of the amplified PHELIX cDNA. In another embodiment, a method of detecting a PHELIX gene in a biological sample comprises first isolating genomic DNA from the sample; amplifying the isolated genomic DNA using PHELIX polynucleotides as sense and antisense primers to amplify the PHELIX gene therein; and detecting the presence of the amplified PHELIX gene. Any number of appropriate sense and antisense probe combinations may be designed from the nucleotide sequences provided for PHELIX (FIG. 2, SEQ ID NO: 2,) and used for this purpose.

The invention also provides assays for detecting the presence of a PHELIX protein in a tissue of other biological sample such as serum, bone, prostate, and other tissues, urine, cell preparations, and the like. Methods for detecting a PHELIX protein are also well known and include, for example, immunoprecipitation, immunohistochemical analysis, Western Blot analysis, molecular binding assays, ELISA, ELIFA and the like. For example, in one embodiment, a method of detecting the presence of a PHELIX protein in a biological sample comprises first contacting the sample with a PHELIX antibody, a PHELIX-reactive fragment thereof, or a recombinant protein containing an antigen binding region of a PHELIX antibody; and then detecting the binding of PHELIX protein in the sample thereto.

Methods for identifying a cell which expresses PHELIX are also provided. In one embodiment, an assay for identifying a cell which expresses a PHELIX gene comprises detecting the presence of PHELIX mRNA in the cell. Methods for the detection of particular mRNAs in cells are well known and include, for example, hybridization assays using complementary DNA probes (such as in situ hybridization using labeled PHELIX riboprobes, Northern blot and related techniques) and various nucleic acid amplification assays (such as RT-PCR using complementary primers specific for PHELIX, and other amplification type detection methods, such as, for example, branched DNA, SISBA, TMA and the like). Alternatively, an assay for identifying a cell which expresses a PHELIX gene comprises detecting the presence of PHELIX protein in the cell or secreted by the cell. Various methods for the detection of proteins are well known in the art and may be employed for the detection of PHELIX proteins and PHELIX expressing cells.

PHELIX expression analysis may also be useful as a tool for identifying and evaluating agents which modulate PHELIX gene expression. For example, PHELIX expression is significantly upregulated in prostate cancer, and may also be expressed in other cancers. Identification of a molecule or biological agent that could inhibit PHELIX expression or over-expression in cancer cells may be of therapeutic value. Such an agent may be identified by using a screen that quantifies PHELIX expression by RT-PCR, nucleic acid hybridization or antibody binding.

ASSAYS FOR DETERMINING PHELIX EXPRESSION STATUS

Determining the status of PHELIX expression patterns in an individual may be used to diagnose cancer and may provide prognostic information useful in defining appropriate therapeutic options. Similarly, the expression status of PHELIX may provide information useful for predicting susceptibility to particular disease stages, progression, and/or tumor aggressiveness. The invention provides methods and assays for determining PHELIX expression status and diagnosing cancers which express PHELIX, such as cancers of the prostate, bladder, ovary and testis. PHELIX expression status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis.

In one aspect, the invention provides assays useful in determining the presence of cancer in an individual, comprising detecting a significant increase in PHELIX mRNA or protein expression in a test cell or tissue sample relative to expression levels in the corresponding normal cell or tissue. The presence of PHELIX mRNA may, for example, be evaluated in tissue samples including but not limited to colon, lung, prostate, pancreas, bladder, breast, ovary, cervix, testis, head and neck, brain, stomach, etc. The presence of significant PHELIX expression in any of these tissues may be useful to indicate the emergence, presence and/or severity of these cancers, since the corresponding normal tissues do not express PHELIX mRNA or express it at lower levels.

In a related embodiment, PHELIX expression status may be determined at the protein level rather than at the nucleic acid level. For example, such a method or assay would comprise determining the level of PHELIX protein expressed by cells in a test tissue sample and comparing the level so determined to the level of PHELIX expressed in a corresponding normal sample. In one embodiment, the presence of PHELIX protein is evaluated, for example, using immunohistochemical methods. PHELIX antibodies or binding partners capable of detecting PHELIX protein expression may be used in a variety of assay formats well known in the art for this purpose.

In addition, peripheral blood may be conveniently assayed for the presence of cancer cells, including but not limited to prostate, bladder and ovarian cancers, using RT-PCR to detect PHELIX expression. The presence of RT-PCR amplifiable PHELIX mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373–384; Ghossein et al., 1995, J. Clin. Oncol. 13: 1195–2000; Heston et al., 1995, Clin. Chem. 41: 1687–1688). RT-PCR assays are well known in the art.

A related aspect of the invention is directed to predicting susceptibility to developing cancer in an individual. In one embodiment, a method for predicting susceptibility to cancer comprises detecting PHELIX mRNA or PHELIX protein in a tissue sample, its presence indicating susceptibility to cancer, wherein the degree of PHELIX mRNA expression present is proportional to the degree of susceptibility. In a specific embodiment, the presence of PHELIX in prostate tissue is examined, with the presence of PHELIX in the sample providing an indication of prostate cancer susceptibility (or the emergence or existence of a prostate tumor). In another specific embodiment, the presence of PHELIX in bladder tissue is examined, with the presence of PHELIX in the sample providing an indication of bladder cancer susceptibility (or the emergence or existence of a bladder tumor). In yet another specific embodiment, the presence of PHELIX in ovary is examined, with the presence of PHELIX providing an indication of susceptibility to (or presence of) an ovarian tumor. In another embodiment, the presence of PHELIX in urine is examined, with the presence of PHELIX therein providing an indication of susceptibility to (or presence of) a PHELIX expressing bladder tumor.

Yet another related aspect of the invention is directed to methods for gauging tumor aggressiveness. In one embodiment, a method for gauging aggressiveness of a tumor comprises determining the level of PHELIX mRNA or PHELIX protein expressed by cells in a sample of the tumor, comparing the level so determined to the level of PHELIX mRNA or PHELIX protein expressed in a corresponding normal tissue taken from the same individual or a normal tissue reference sample, wherein the degree of PHELIX mRNA or PHELIX protein expression in the tumor sample relative to the normal sample indicates the degree of aggressiveness. In a specific embodiment, aggressiveness of prostate, bladder, ovarian or testicular tumors is evaluated by determining the extent to which PHELIX is expressed in the tumor cells, with higher expression levels indicating more aggressive tumors.

Methods for detecting and quantifying the expression of PHELIX mRNA or protein are described herein and use standard nucleic acid and protein detection and quantification technologies well known in the art. Standard methods for the detection and quantification of PHELIX mRNA include in situ hybridization using labeled PHELIX riboprobes, Northern blot and related techniques using PHELIX polynucleotide probes, RT-PCR analysis using primers specific for PHELIX, and other amplification type detection methods, such as, for example, branched DNA, SISBA, TMA and the like. In a specific embodiment, semi-quantitative RT-PCR may be used to detect and quantify PHELIX mRNA expression as described in the Examples which follow. Any number of primers capable of amplifying PHELIX may be used for this purpose, including but not limited to the various primer sets specifically described herein. Standard methods for the detection and quantification of protein may be used for this purpose. In a specific embodiment, polyclonal or monoclonal antibodies specifically reactive with the wild-type PHELIX protein may be used in an immunohistochemical assay of biopsied tissue.

THERAPEUTIC METHODS AND COMPOSITIONS

The identification of PHELIX as a normally testis-specific protein that is also expressed in cancers of the prostate, bladder, ovary and testis (and possibly other cancers), opens a number of therapeutic approaches to the treatment of such cancers. As discussed above, it is possible that PHELIX functions as a transcription factor involved in activating tumor-promoting genes or repressing genes that block tumorigenesis.

Accordingly, therapeutic approaches aimed at inhibiting the activity of the PHELIX protein are expected to be useful for patients suffering from prostate cancer, bladder cancer, ovarian cancer and testicular cancer, as well as and other cancers expressing PHELIX. These therapeutic approaches generally fall into two classes. One class comprises various methods for inhibiting the binding or association of the PHELIX protein with its binding partner or with others proteins. Another class comprises a variety of methods for inhibiting the transcription of the PHELIX gene or translation of PHELIX mRNA.

A. Therapeutic Methods—Inhibition of PHELIX Protein Function

Within the first class of therapeutic approaches, the invention includes various methods and compositions for inhibiting the binding of PHELIX to its binding partner or its association with other protein(s) as well as methods for inhibiting PHELIX function.

A.1. Therapeutic Inhibition of PHELIX with Intracellular Antibodies

In one approach, recombinant vectors encoding single chain antibodies which specifically bind to PHELIX may be introduced into PHELIX expressing cells via gene transfer technologies, wherein the encoded single chain anti-PHELIX antibody is expressed intracellularly, binds to PHELIX protein, and thereby inhibits its function. Methods for engineering such intracellular single chain antibodies are well known. Such intracellular antibodies, also known as "intrabodies", may be specifically targeted to a particular compartment within the cell, providing control over where the inhibitory activity of the treatment will be focused. This technology has been successfully applied in the art (for review, see Richardson and Marasco, 1995, TIBTECH vol.13). Intrabodies have been shown to virtually eliminate the expression of otherwise abundant cell surface receptors. See, for example, Richardson et al., 1995, Proc. Natl. Acad. Sci. USA 92: 3137–3141; Beerli et al., 1994, J. Biol. Chem. 289: 23931–23936; Deshane et al., 1994, Gene Ther. 1: 332–337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constant region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In one embodiment, intrabodies may be used to capture PHELIX in the nucleus, thereby preventing its activity within the nucleus. Nuclear targeting signals may be engineered into such PHELIX intrabodies in order to achieve the desired targeting. Such PHELIX intrabodies may be designed to bind specifically to a particular PHELIX domain, such as, for example, the bHLH domain of the PHELIX protein. In another embodiment, cytosolic intrabodies which specifically bind to the PHELIX protein may be used to prevent PHELIX from gaining access to the nucleus, thereby preventing it from exerting any biological activity within the nucleus (e.g., preventing PHELIX from forming transcription complexes with other factors).

In order to specifically direct the expression of such intrabodies to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

A.2. Therapeutic Inhibition of PHELIX with Recombinant Proteins

In another approach, recombinant molecules which are capable of binding to PHELIX thereby preventing PHELIX from accessing/binding to its binding partner(s) or associating with other protein(s) are used to inhibit PHELIX function. Such recombinant molecules may, for example, contain the reactive part(s) of a PHELIX specific antibody molecule. In a particular embodiment, the PHELIX binding domain of a PHELIX binding partner may be engineered into a dimeric fusion protein comprising two PHELIX ligand binding domains linked to the Fc portion of a human IgG, such as human IgG1. Such IgG portion may contain, for example, the $C_H2$ and $C_H3$ domains and the hinge region, but not the $C_H1$ domain. Such dimeric fusion proteins may be administered in soluble form to patients suffering from a cancer associated with the expression of PHELIX, including but not limited to prostate and bladder cancers, where the dimeric fusion protein specifically binds to PHELIX thereby blocking PHELIX interaction with a binding partner. Such dimeric fusion proteins may be further combined into multimeric proteins using known antibody linking technologies.

B. Therapeutic Methods Based on Inhibition of PHELIX Transcription or Translation Within the second class of therapeutic approaches, the invention provides various methods and compositions for inhibiting the transcription of the PHELIX gene. Similarly, the invention also provides methods and compositions for inhibiting the translation of PHELIX mRNA into protein.

In one approach, a method of inhibiting the transcription of the PHELIX gene comprises contacting the PHELIX gene with a PHELIX antisense polynucleotide. In another approach, a method of inhibiting PHELIX mRNA translation comprises contacting the PHELIX mRNA with an antisense polynucleoude. In another approach, a PHELIX specific ribozyme may be used to cleave the PHELIX message, thereby inhibiting translation. Such antisense and ribozyme based methods may also be directed to the regulatory regions of the PHELIX gene, such as the PHELIX promoter and/or enhancer elements. Similarly, proteins capable of inhibiting a PHELIX gene transcription factor may be used to inhibit PHELIX mRNA transcription. The various polynucleotides and compositions useful in the aforementioned methods have been described above. The use of antisense and ribozyme molecules to inhibit transcription and translation is well known in the art.

Other factors which inhibit the transcription of PHELIX through interfering with PHELIX transcriptional activation may also be useful for the treatment of cancers expressing PHELIX. Similarly, factors which are capable of interfering with PHELIX processing may be useful for the treatment of cancers expressing PHELIX. Cancer treatment methods utilizing such factors are also within the scope of the invention.

C. General Considerations

Gene transfer and gene therapy technologies may be used for delivering therapeutic polynucleotide molecules to tumor cells synthesizing PHELIX (i.e., antisense, ribozyme, polynucleotides encoding intrabodies and other PHELIX inhibitory molecules). A number of gene therapy approaches are known in the art. Recombinant vectors encoding PHELIX antisense polynucleotides, ribozymes, factors capable of interfering with PHELIX transcription, and so forth, may be delivered to target tumor cells using such gene therapy approaches.

The above therapeutic approaches may be combined with chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of PHELIX to a binding partner, etc.

In vivo, the effect of a PHELIX therapeutic composition may be evaluated in a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402–408). For Example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Various bladder carcinoma models are known (see, for example, Russell et al., 1986, Cancer Res. 46: 2035–2040; Raghavan et al., 1992, Semin. Surg. Oncol. 8: 279–284; Rieger et al., 1995, Br. J. Cancer 72: 683–690; Oshinsky et al., 1995, J. Urol. 154: 1925–1929). Efficacy may be predicted using assays which measure inhibition of tumor formation, tumor regression or metastasis, and the like. See, also, the Examples below.

In vivo assays which qualify the promotion of apoptosis may also be useful in evaluating potential therapeutic compositions. In one embodiment, xenografts from bearing mice treated with the therapeutic composition may be examined for the presence of apoptotic foci and compared to un-treated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions comprising a carrier suitable for the desired delivery method. Suitable carriers include any material which when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

CANCER VACCINES

The invention further provides prostate cancer vaccines comprising a PHELIX protein or fragment thereof, as well as DNA based vaccines. In view of the testis-restricted expression of PHELIX in normal human tissues (and the existence of the testis-blood barrier), PHELIX cancer vaccines are expected to be effective at specifically preventing and/or treating PHELIX expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231–237; Fong et al., 1997, J. Immunol. 159: 3113–3117). Such methods can be readily practiced by employing a PHELIX protein, or fragment thereof, or a PHELIX-encoding nucleic acid molecule and recombinant vectors capable of expressing and appropriately presenting the PHELIX immunogen.

For example, viral gene delivery systems may be used to deliver a PHELIX-encoding nucleic acid molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658–663). Non-viral delivery systems may also be employed by using naked DNA encoding a PHELIX protein or fragment thereof introduced into the patient (e.g., intramuscularly) to induce an anti-tumor response. In one embodiment, the full-length human PHELIX cDNA may be employed. In another embodiment, PHELIX nucleic acid molecules encoding specific cytotoxic T lymphocyte (CTL) epitopes may be employed. CTL epitopes can be determined using specific algorithms (e.g., Epimer, Brown University) to identify peptides within a PHELIX protein which are capable of optimally binding to specified HLA alleles.

Various ex vivo strategies may also be employed. One approach involves the use of dendritic cells to present PHELIX antigen to a patient's immune system. Dendritic cells express MHC class I and II, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65–69; Murphy et al., 1996, Prostate 29: 371–380). Dendritic cells can be used to present PHELIX peptides to T cells in the context of MHC class I and II molecules. In one embodiment, autologous dendritic cells are pulsed with PHELIX peptides capable of binding to MHC molecules. In another embodiment, dendritic cells are pulsed with the complete PHELIX protein. Yet another embodiment involves engineering the overexpression of the PHELIX gene in dendritic cells using various implementing vectors known in the art, such as adenovirus (Arthur et al., 1997, Cancer Gene Ther. 4: 17–25), retrovirus (Henderson et al., 1996, Cancer Res. 56: 3763–3770), lentivirus, adeno-associated virus, DNA transfection (Ribas et al., 1997, Cancer Res. 57: 2865–2869), and tumor-derived RNA transfection (Ashley et al., 1997, J. Exp. Med. 186: 1177–1182). Cells expressing PHELIX may also be engineered to express immune modulators, such as GM-CSF, and used as immunizing agents.

Anti-idiotypic anti-PHELIX antibodies can also be used in anti-cancer therapy as a vaccine for inducing an immune response to cells expressing a PHELIX protein. Specifically, the generation of anti-idiotypic antibodies is well known in the art and can readily be adapted to generate anti-idiotypic anti-PHELIX antibodies that mimic an epitope on a PHELIX protein (see, for example, Wagner et al., 1997, Hybridoma 16: 33–40; Foon et al., 1995, J Clin Invest 96: 334–342; Herlyn et al., 1996, Cancer Immunol Immunother 43: 65–76). Such an anti-idiotypic antibody can be used in cancer vaccine strategies.

Genetic immunization methods may be employed to generate prophylactic or therapeutic humoral and cellular immune responses directed against cancer cells expressing PHELIX. Constructs comprising DNA encoding a PHELIX protein/immunogen and appropriate regulatory sequences may be injected directly into muscle or skin of an individual, such that the cells of the muscle or skin take-up the construct and express the encoded PHELIX protein/immunogen. Expression of the PHELIX protein immunogen results in the generation of prophylactic or therapeutic humoral and cellular immunity against prostate cancer. Various prophylactic and therapeutic genetic immunization techniques known in the art may be used (for review, see information and references published at Internet address www.genweb.com).

KITS

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe which is or can be detectably labeled. Such probe may be an antibody or polynucleotide specific for a PHELIX protein or a PHELIX gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

EXAMPLES

Various aspects of the invention are further described and illustrated by way of the several examples which follow, none of which are intended to limit the scope of the invention.

Example 1

Isolation of cDNA Fragment of PHELIX Gene

Materials and Methods

LAPC Xenografts

LAPC xenografts were obtained from Dr. Charles Sawyers (UCLA) and generated as described (Klein et al, 1997, Nature Med. 3: 402–408). Androgen dependent and independent LAPC-4 xenografts LAPC-4 AD and AI, respectively) and LAPC-9 AD xenografts were grown in male SCID mice and were passaged as small tissue chunks in recipient males. LAPC-4 AI xenografts were derived from LAPC-4 AD tumors. Male mice bearing LAPC-4 AD tumors were castrated and maintained for 2–3 months. After the LAPC-4 tumors re-grew, the tumors were harvested and passaged in castrated males or in female SCID mice.

Cell Lines

Human cell lines (e.g., HeLa) were obtained from the ATCC and were maintained in DMEM with 5% fetal calf serum.

RNA Isolation

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides

The following HPLC purified oligonucleotides were used.

DPNCDN (cDNA synthesis primer): (SEQ ID NO. 5)

5'TTTTGATCAAGCTT$_{30}$3'

Adaptor 1:

5'CTAATACGACTCACTATAGGGCTC-GAGCGGCCGCCCGGGCAG3' (SEQ ID NO. 6)

3'GGCCCGTCCTAG5' (SEQ ID NO. 15)

Adaptor 2

5'GTAATACGACTCACTATAGGGCAGCGTG-GTCGCGGCCGAG3' (SEQ ID NO. 7)

3'CGGCTCCTAG5' (SEQ ID NO. 16)

PCR primer 1 (SEQ ID NO. 8):

5'CTAATACGACTCACTATAGGGC3'

Nested primer (NP)1 (SEQ ID NO. 9):

5'TCGAGCGGCCGCCGGGCAGGA3'

Nested primer (NP)2 (SEQ ID NO. 10):

5'AGCGTGGTCGCGGCCGAGGA3'

Suppression Subtractive Hybridization

Suppression Subtractive Hybridization (SSH) was used to identify cDNAs corresponding to genes which may be over-expressed in prostate cancer.

Double stranded cDNAs corresponding to the LAPC-4 AI xenograft (tester) and the LAPC-4 AD xenograft (driver) were synthesized from 2 μg of poly(A)+ RNA isolated from xenograft tissue, as described above, using CLONTECH's PCR-Select cDNA Subtraction Kit and 1 ng of oligonucleotide DPNCDN as primer. First- and second- strand synthesis were carried out as described in the Kit's user manual protocol (CLONTECH Protocol No. PT1117-1, Catalog No. K1804-1). The resulting cDNA was digested with Dpn II for 3 hrs. at 37° C. Digested cDNA was extracted with phenol/chloroform (1:1) and ethanol precipitated.

Driver cDNA (LAPC-4 AD) was generated by combining in a 1:1 ratio Dpn II digested LAPC-4 AD cDNA with a mix of digested cDNAs derived from human benign prostatic hyperplasia (BPH), the human cell lines HeLa, 293, A431, Colo205, and mouse liver.

Tester cDNA (LAPC-4 AI) was generated by diluting 1 μl of Dpn II digested LAPC-4 AI cDNA (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2- ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification. Cloning and Sequencing of Gene Fragments Generated from SSH

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10×reaction buffer (CLONTECH) and 0.5 μl 50×Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10–12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis

First strand cDNAs were generated from 1 µg of mRNA with oligo (dT)12–18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200 µl with water prior to normalization. First strand cDNAs from 16 different normal human tissues were obtained from Clontech.

Normalization of the first strand cDNAs were from multiple tissues was performed by using the primers 5'atatcgcgcgctcgtcgtcgacaa3' (SEQ ID NO: 13) and 5'agccacacgcagctcattgtagaagg3' (SEQ ID NO: 14) to amplify β-actin. First strand cDNA (5 µl) was amplified in a total volume of 50 µl containing 0.4 µM primers, 0.2 µM each dNTPs, 1XPCR buffer (Clontech, 10 mM Tris-HCL, 1.5 mM MgCl$_2$, 50 mM KCI, pH 8.3) and 1X Klentaq DNA polymerase (Clontech). Five µl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the PHELIX gene, 5 µl of normalized first strand cDNA was analyzed by PCR using 25, 30, and 35 cycles of amplification using the following primer pairs, which were designed with the assistance of (MIT; for details, see, www.genome.wi.mit.edu):

5'-CTG CGT ACT CTC TTG CCG TAT GT-3' (SEQ ID NO. 11)

5'-GCT CAA TGG GTG TTT GTT GTT TCT-3' (SEQ ID NO. 12)

Semi quantitative expression analysis was achieved by comparing the PCR products at cycle numbers that give light band intensities.

Results

Suppression subtractive hybridization (SSH) was used to identify novel prostate and prostate cancer specific genes by comparing cDNAs from androgen dependent LAPC-4 xenograft with cDNAs derived from androgen independent LAPC-4 xenograft, as described above. This strategy resulted in the identification of several genes up-regulated in prostate cancer.

One of the SSH clones, comprising about 437 bp, initially showed no homology to any known gene, and was designated 22P4G9. This clone represents a fragment of the full length cDNA encoding PHELIX as shown in FIG. 2 (SEQ ID NO. 1) (see, also, Example 2).

Initial expression analysis by RT-PCR showed expression in the LAPC-4 xenografts (both AI and AD) and very low level expression in normal prostate (FIG. 7, Panel A). In addition, further RT-PCR expression analysis of first strand cDNAs from 16 normal tissues detected expression of the PHELIX gene only in testis tissue at 30 cycles of amplification (FIG. 7, panels B and C). Northern blot and dot blot analysis confirms the testis-specific expression profile of PHELIX, as described in Example 3, below.

Example 2

Isolation of Full Length PHELIX Encoding cDNA

A full length 22P4G9/PHELIX clone (GTP1C12) of 2130 base pairs was cloned from a normal testis cDNA library (GIBCO-BRL Gene trapper). The cDNA encodes an open reading frame (ORF) of 405 amino acids (FIG. 2) (SEQ ID NO. 2). Sequence analysis revealed the presence of a bHLH domain with some similarity to the bHLH domains of Max and Mxi (FIG. 3), which led to naming the encoded protein PHELIX for Prostate cancer HELIX-loop-helix protein. In addition, computer analysis of the PHELIX amino acid sequence (using PSORT II) shows two nuclear localization sequences, indicating that the PHELIX protein is nuclear. A schematic representation of the PHELIX structure is shown in FIG. 1.

The full length PHELIX cDNA (pPHELIX, clone GTP1C12) was deposited with the American Type Culture Collection, 10801 University Boulevard, Manassas, Va. 20110-2209, on Oct. 22, 1998 and has been accorded ATCC accession number 98956.

Example 3

PHELIX Gene Expression Analysis—Testis Specific in Normal Tissues

PHELIX mRNA expression in normal human tissues was first analyzed by Northern blotting of two multiple tissue blots (Clontech; Palo Alto, Calif.), comprising a total of 16 different normal human tissues, using labeled 22P4G9 SSH fragment (Example 1) as a probe. RNA samples were quantitatively normalized with a β-actin probe. The results of this analysis are shown in FIG. 4. Expression of a 3 kb transcript was only detected in normal testis.

PHELIX expression in normal tissues was further analyzed using a multi-tissue RNA dot blot containing 76 different samples (representing mainly normal tissues as well as a few cancer cell lines) demonstrated strong expression of PHELIX only in testis (FIG. 5).

Example 4

PHELIX Expression in Prostate Cancer and Other Cancers

To analyze PHELIX expression in cancer tissues and cell lines, Northern blot analysis was performed on RNA derived from the LAPC prostate cancer xenografts as well as a panel of prostate cancer and other cancer cell lines. The results (FIG. 6) show high levels of PHELIX expression in LAPC-4 AD and LAPC-4 AI, with lower levels detected several cancer cell lines derived from prostate (TsuPr1), bladder (HT1197), testis (NCCIT, TERA-1), and ovary (OV-1063, PA-1). The strongest expression was observed in the androgen independent LAPC-4 xenograft, occurring at significantly higher levels than in the androgen dependent LAPC-4 xenograft, suggesting a potential role of the PHELIX gene in the transition to the androgen independent phenotype. These results suggest that PHELIX is a very testis specific gene that is up-regulated in some cancers. Moreover, the very high level expression seen in androgen independent prostate cancer may provide a basis for predicting, detecting and/or monitoring the transition to androgen independence.

Example 5

Generation of PHELIX Polyclonal Antibodies

In order to generate reagents that specifically bind to PHELIX, a 15 mer peptide was designed from the PHELIX coding region. Specifically, the peptide HSSKEKLRRE-RIKYC (positions 140–154 of SEQ. ID. NO: 2) was conjugated to keyhole limpet hemocyanin (KLH) and used to immunize a rabbit. Rabbit serum was tested for reactivity with a recombinant PHELIX protein, as described in Example 6, below. The rabbit polyclonal antiserum demonstrated specifically for PHELIX and may therefore be useful for assessing the expression of PHELIX in patient samples.

Example 6

Production of Recombinant PHELIX in a Mammalian Systems

Figure 8:
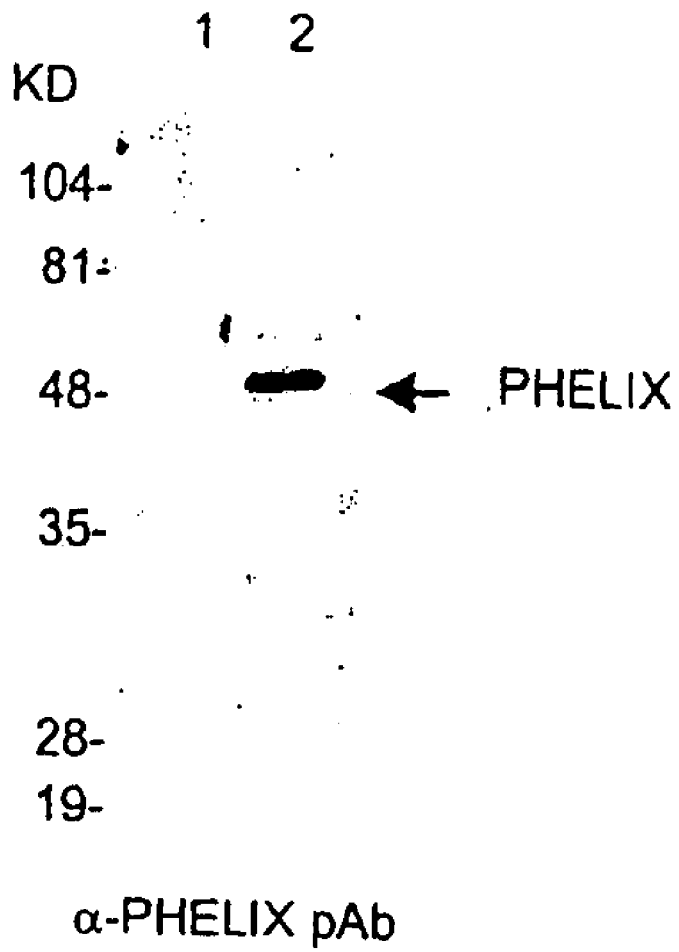
FIG. 8. Western blot detection of recombinant human PHELIX protein in lysates of 293T cells transfected with a His-tagged PHELIX cDNA using anti-PHELIX rabbit polyclonal antiserum.

To express recombinant PHELIX, the full length PHELIX cDNA was cloned into an expression vector that provides a 6His tag at the carboxyl-terminus (pCDNA 3.1 myc-his, InVitrogen). The construct was transfected into 293T cells. Transfected 293T cell lysates were probed with the anti-PHELIX serum described in Example 5 above in a Western blot. The results show that the polyclonal serum recognizes a 48 kilodalton (KD) protein only in the PHELIX transfected cells, and not in the control vector transfected cells (FIG. 8).

The PHELIX gene was also subcloned into the retroviral expression vector pSRαMSVtkneo and used to establish PHELIX expressing cell lines as follows. The PHELIX coding sequence (from translation initiation ATG to the termination codons) was amplified by PCR using ds cDNA template from PHELIX clone GTP1C12. The 5' end primer for the PCR reaction contained the Kozak sequence and 19 nucleotides complementary to the 5' end of the cDNA beginning with codon ATG. The 3' end primer for the PCR reaction contained 19 nucleotides complementary to the 3' end of the ds cDNA, ending with the termination codons, TGA,TAA in tandem, followed by sequences with the Xba 1 restriction site. The PCR product was subcloned into pSRαMSVtkneo via the EcoR1(blunt-ended) and Xba 1 restriction sites on the vector and transformed into DH5α competent cells. Colonies were picked to screen for clones with unique internal restriction sites on the cDNA. The positive clone is confirmed by sequencing of the cDNA insert. Retroviruses were made and used for infection and generation of the following cell lines: 3T3CL7/Phelix, PC3/Phelix, and LnCap/PHELIX.

Example 7

Production of Recombinant PHELIX in a Baculovirus System

To generate recombinant PHELIX protein in a baculovirus expression system, PHELIX cDNA is cloned into the baculovirus transfer vector pBlueBac 4.5 (Invitrogen) which provides a His-tag at the N-terminus Specifically, pBlueBac-PHELIX is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant PHELIX protein is then generated by infection of HighFive insect cells (InVitrogen) with the purified baculovirus. Recombinant PHELIX protein may be detected using anti-PHELIX rabbit polyclonal antibody of Example 5 or a similar PHELIX-specific antibody. PHELIX protein may be purified and used in various cell based assays or as immunogen to generate polyclonal and monoclonal antibodies specific for PHELIX.

Example 8

Generation of PHELIX Monoclonal Antibodies

In order to generate PHELIX monoclonal antibodies, a glutathione-S-transferase (GST) fusion protein encompassing the PHELIX protein is synthesized and used as immunogen. Balb C mice are initially immunized intraperitoneally with 200 µg of the GST-PHELIX fusion protein mixed in complete Freund's adjuvant. Mice are subsequently immunized every 2 weeks with 75 µg of GST-PHELIX protein mixed in Freund's incomplete adjuvant for a total of 3 immunizations. Reactivity of serum from immunized mice to full length PHELIX protein is monitored by ELISA using a partially purified preparation of HIS-tagged PHELIX protein expressed from 293T cells (Example 6). Mice showing the strongest reactivity are rested for 3 weeks and given a final injection of fusion protein in PBS and then sacrificed 4 days later. The spleens of the sacrificed mice are then harvested and fused to SPO/2 myeloma cells using standard procedures (Harlow and Lane, 1988). Supernatants from growth wells following HAT selection are screened by ELISA and Western blot to identify PHELIX specific antibody producing clones.

The binding affinity of a PHELIX monoclonal antibody may be determined using standard technology. Affinity measurements quantify the strength of antibody to epitope binding and may be used to help define which PHELIX monoclonal antibodies are preferred for diagnostic or therapeutic use. The BIAcore system (Uppsala, Sweden) is a preferred method for determining binding affinity. The BIAcore system uses surface plasmon resonance (SPR, Welford K. 1991, Opt. Quant. Elect 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 9

Chromosomal Mapping of the PHELIX Gene

The chromosomal localization of PHELIX was determined using the GeneBridge4 radiation hybrid panel (Walter et al., 1994, Nat. Genetics 7:22) (Research Genetics, Huntsville Ala.). The following PCR primers were used to localize PHELIX:

22P4G9.1 5'-CTG CGT ACT CTC TTG CCG TAT GT-3' (SEQ ID NO: 11)

22P4G9.2 5'-GCT CAA TGG GTG TTT GTT GTT TCT-3' (SEQ ID NO: 12)

The resulting mapping vector for the 93 radiation hybrid panel DNAs was: 110001100000000000000000000110010000000011101100000010100000011000001011110000000000000000101.

This vector and the mapping program at http://www-genome.wi.mit.edu/cgi-bin/contig/rhmapper.pl placed PHELIX on chromosome 13*q*13.1–13.3.

Example 10

Identification of Potential Signal Transduction Pathways

To determine whether PHELIX directly or indirectly activates known signal transduction pathways in cells, luciferase (luc) based transcriptional reporter assays are carried out in cells expressing PHELIX. These transcriptional reporters contain consensus binding sites for known transcription factors which lie downstream of well characterized signal transduction pathways. The reporters and examples of there associated transcription factors, signal transduction pathways, and activation stimuli are listed below.

1. NFkB-luc, NFkB/Rel; lk-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress PHELIX-mediated effects may be assayed in cells showing mRNA expression, such as the PHELIX-expressing cancer cell lines shown in FIG. 6. Luciferase reporter plasmids may be introduced by lipid mediated transfection (TFX-50, Promega). Luciferase activity, an indicator of relative transcriptional activity, is measured by incubation of cells extracts with luciferin substrate and luminescence of the reaction is monitored in a luminometer.

Example 11

In Vitro Assays of PHELIX Function

The expression of PHELIX in prostate cancer and other cancers suggests a functional role in tumor progression. It is possible that PHELIX functions as a transcription factor involved in activating genes involved in tumorigenesis or repressing genes that block tumorigenesis. PHELIX function can be assessed in mammalian cells using in vitro approaches. For mammalian expression, PHELIX can be cloned into a number of appropriate vectors, including pCDNA 3.1 myc-His-tag (Example 6) and the retroviral vector pSRαtkneo (Muller et al., 1991, MCB 11:1785). Using such expression vectors, PHELIX can be expressed in several cell lines, including PC-3, NIH 3T3, LNCaP and 293T. Expression of PHELIX can be monitored using anti-PHELIX antibodies (see Examples 5 and 8).

Mammalian cell lines expressing PHELIX can be tested in several in vitro and in vivo assays, including cell proliferation in tissue culture, activation of apoptotic signals, tumor formation in SCID mice, and in vitro invasion using a membrane invasion culture system (MICS) (Welch et al., Int. J. Cancer 43: 449–457). PHELIX cell phenotype is compared to the phenotype of cells that lack expression of PHELIX.

Cell lines expressing PHELIX can also be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells. Cell lines analyzed include parental and PHELIX overexpressing PC3, 3T3 and LNCaP cells. To assay whether PHELIX has chemoattractant properties, parental indicator cells are monitored for passage through the porous membrane toward a gradient of PHELIX conditioned media compared to control media. This assay may also be used to qualify and quantify specific neutralization of the PHELIX induced effect by candidate cancer therapeutic compositions.

Example 12

In Vivo Assay for PHELIX Tumor Growth Promotion

The effect of the PHELIX protein on tumor cell growth may be evaluated in vivo by gene overexpression in tumor-bearing mice. For example, SCID mice can be injected SQ on each flank with $1 \times 10^6$ of either PC3, TSUPR1, or DU145 cells containing tkNeo empty vector or PHELIX. At least two strategies may be used: (1) Constitutive PHELIX expression under regulation of an LTR promoter, and (2) Regulated expression under control of an inducible vector system, such as ecdysone, tet, etc. Tumor volume is then monitored at the appearance of palpable tumors and followed over time to determine if PHELIX expressing cells grow at a faster rate. Additionally, mice may be implanted with $1 \times 10^6$ of the same cells orthotopically to determine if PHELIX has an effect on local growth in the prostate or on the ability of the cells to metastasize, specifically to lungs, lymph nodes, and bone marrow.

The assay is also useful to determine the PHELIX inhibitory effect of candidate therapeutic compositions, such as for example, PHELIX intrabodies, PHELIX antisense molecules and ribozymes.

Example 13

Western Analysis of PHELIX Expression in Subcellar Fractions

To determine the subcellular localization of PHELIX protein, 293T cells were transfected with an expression vector encoding HIS-tagged PHELIX (pcDNA 3.1 MYC/HIS, Invitrogen)(see Example 6, above). The transfected cells were harvested and subjected to a differential subcellular fractionation protocol as previously described (Pemberton, P. A. et al, 1997, J of Histochemistry and Cytochemistry, 45:1697–1706.) This protocol separates the cell into fractions enriched for nuclei, heavy membranes (lysosomes, peroxisomes, and mitochondria), light membranes (plasma membrane and endoplasmic reticulum), and soluble proteins.

A whole cell lysate or subcellular fractions obtained by differential centrifugation of the transfected 293T cells were separated by SDS-PAGE and subjected to Western blot analysis. The blots were then developed with anti-rabbit-HRP conjugated secondary Ab and visualized by enhanced chemiluminescense. The transfected cells were lysed in 2 mls of buffer and each subcellular fraction lane represents approximately $\frac{1}{60}^{th}$ (by volume) of the starting material.

The results are shown in FIG. 9. Both the anti-HIS antibody or the anti-PHELIX polyclonal antibody localize PHELIX predominantly within the nuclear fraction and to a lesser extent within the heavy membrane fraction (FIG. 9). The whole cell lysate lane represents approximately $\frac{1}{60}^{th}$ of the starting material (FIG. 9).

Throughout this application, various publications are referenced within parentheses. The disclosures of these publications are hereby incorporated by reference herein in their entireties.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. An isolated PHELIX protein having the amino acid sequence as shown in FIG. 2 (SEQ ID NO: 2).

2. The PHELIX protein of claim 1, further comprising a heterologous polypeptide.

3. An isolated fragment of the amino acid sequence of SEQ ID NO: 2 of at least 15 contiguous amino acids of said sequence comprising amino acid residues 140–154 of SEQ ID NO: 2 wherein the fragment is recognized by an antibody that specifically binds a PHELIX protein having the amino acid sequence of SEQ ID NO: 2.

4. The PHELIX polypeptide of claim 3, further comprising a heterologous polypeptide.

5. An isolated polypeptide that is at least 90% identical to the amino acid sequence of SEQ ID NO: 2 over the entire length of SEQ ID NO: 2 and wherein any amino acid substitutions are conservative substitutions wherein the polypeptide is recognized by an antibody that specifically binds a PHELIX protein having the amino acid sequence of SEQ ID NO: 2.

6. The PHELIX polypeptide of claim 5, further comprising a heterologous polypeptide.

7. A PHELIX polypeptide produced by culturing a host cell that contains an expression vector that comprises an isolated polynucleotide selected from the group consisting of:

(a) a polynucleotide having the sequence as shown in FIG. 2 (SEQ ID NO: 1), wherein T can also be U;

(b) a polynucleotide having the sequence as shown in FIG. 2 (SEQ ID NO: 1), from nucleotide residue number 735 through nucleotide residue number 1949, wherein T can also be U;

(c) a polynucleotide encoding a PHELIX polypeptide whose sequence is encoded by the cDNA contained in the plasmid as deposited with American Type Culture Collection as Accession No. 98956; and (d) a polynucleotide encoding a PHELIX protein having the amino acid sequence shown in FIG. 2 (SEQ ID NO: 2).

8. The PHELIX polypeptide of claim 7, further comprising a heterologous polypeptide.

9. A composition for eliciting formation of antibodies directed to a cell that expresses a PHELIX protein, the composition comprising:

(a) a PHELIX protein according to claim 1; and (b) a pharmaceutically acceptable carrier.

10. A composition for eliciting formation of antibodies directed to a cell that expresses a PHELIX protein, the composition comprising:

(a) an immunogenic portion of a PHELIX protein according to claim 3; and (b) a pharmaceutically acceptable carrier.

\* \* \* \* \*